US007352453B2

(12) United States Patent
Mieher et al.

(10) Patent No.: US 7,352,453 B2
(45) Date of Patent: Apr. 1, 2008

(54) METHOD FOR PROCESS OPTIMIZATION AND CONTROL BY COMPARISON BETWEEN 2 OR MORE MEASURED SCATTEROMETRY SIGNALS

(75) Inventors: Walter D. Mieher, Los Gatos, CA (US); Chris A. Mack, Austin, TX (US); Matt Hankinson, San Jose, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 490 days.

(21) Appl. No.: 10/760,149

(22) Filed: Jan. 17, 2004

(65) Prior Publication Data

US 2004/0190008 A1 Sep. 30, 2004

Related U.S. Application Data

(60) Provisional application No. 60/441,048, filed on Jan. 17, 2003.

(51) Int. Cl.
*G01B 9/00* (2006.01)

(52) U.S. Cl. ...................................................... 356/125

(58) Field of Classification Search ..................... None
See application file for complete search history.

(56) References Cited

U.S. PATENT DOCUMENTS 4,908,656 A 3/1990 Suwa et al.
5,607,800 A 3/1997 Ziger
5,629,772 A 5/1997 Ausschnitt
5,773,174 A 6/1998 Koizumi et al.
5,790,254 A 8/1998 Ausschnitt
5,902,703 A 5/1999 Leroux et al.
5,936,738 A 8/1999 Liebmann et al.
5,965,309 A 10/1999 Ausschnitt et al.
5,976,740 A 11/1999 Ausschnitt et al.
6,016,684 A 1/2000 Scheer et al.
6,063,531 A 5/2000 Singh et al.
6,304,999 B1 10/2001 Toprac et al.
6,429,930 B1 * 8/2002 Littau et al. ................ 356/124
6,433,878 B1 8/2002 Niu et al.
6,466,314 B1 * 10/2002 Lehman ................... 356/237.1
6,483,580 B1 11/2002 Xu et al.
6,485,872 B1 11/2002 Rosenthal et al.
6,501,534 B1 12/2002 Singh et al.
6,513,151 B1 1/2003 Erhardt et al.
6,559,953 B1 * 5/2003 Davids ....................... 356/521
6,614,540 B1 * 9/2003 Stirton ....................... 356/630
6,650,422 B2 * 11/2003 Singh et al. ................ 356/601
6,673,638 B1 1/2004 Bendik et al.
6,778,275 B2 8/2004 Bowes
6,879,406 B1 * 4/2005 Rangarajan et al. ........ 356/625
6,884,552 B2 * 4/2005 Mieher et al. .............. 356/401

(Continued)

OTHER PUBLICATIONS

Junwei Bao, "A Lithography Focus Monitor Based on Scattering from 2D Gratings", downloaded May 22, 2002, http://buffy.eecs.berkeley.edu/IRO/Summary/99abstracts/junwei.1.html.

(Continued)

*Primary Examiner*—Gregory J. Toatley, Jr.
*Assistant Examiner*—Juan D Valentin, II
(74) *Attorney, Agent, or Firm*—Beyer Weaver LLP

(57) ABSTRACT

A method for determining one or more process parameter settings of a photolithographic system is disclosed.

33 Claims, 27 Drawing Sheets

U.S. PATENT DOCUMENTS

| | | | | |
|---|---|---|---|---|
| 6,982,793 | B1 | 1/2006 | Yang et al. | |
| 7,079,235 | B2 * | 7/2006 | Lehman | 356/237.1 |
| 2003/0048458 | A1 * | 3/2003 | Mieher et al. | 356/601 |
| 2004/0114132 | A1 * | 6/2004 | Den Boef et al. | 356/124 |
| 2004/0169861 | A1 | 9/2004 | Meiher et al. | |

OTHER PUBLICATIONS

Junwei Bao., "A Spectral Scatterometry-Based Pilot Inspector", downloaded May 22, 2002, http://buffy.eecs.berkeley.edu/IRO/Summary/98abstracts/junwei.3.html.

Edgar et al., "Simultaneous Identification of Focus and Exposure Drifts in Control of Photolithography CD", downloaded May 22, 2002, Technical Program paper Detail—AIChE.

Ralph Foong, "Characterizing the Sensitivity of Spectral Scatterometry", Downloaded May 30, 2002, http://buffy.eecs.berkeley.edu/IRO/Summary/00abstracts/foong.1.html.

Moers et al., "Application of the aberration ring test (ARTEMIS™) to Determine lens Quality and Predict its Lithographic Performance", Proceedings of SPIE vol. 4346 (2001).

School et al., "Printing 130nm DRAM Isolation Pattern: Zernike Correlation and Tool Improvement", Proceedings of SPIE vol. 4346 (2001).

Verhaegen et al., "CD Control for Two-Dimensional Features in Future Technology Nodes", Proceedings of SPIE, vol. 4346 (2001).

"Metrology for the Future", European Semiconductor, Aug. 2001.

"2.1 Some Fundamental Considerations", Downloaded May 22, 2002, www.iue.tuwien.ac.at/publications/PhD%20theses/Kirchauer/node.html.

"3.2.1 Focus Effects and Process Window", Downloaded May 22, 2002, www.iue.tuwien.ac.at/publications/PhD%20theses/Kirchauer/node41.html.

Mieher et al., "Spectroscopic CD Metrology for Sub-100nm Lithography Process Control", Proceedings of SPIE vol. 4689 (2002).

Xinhui Niu, "Spectral Scatterometry for CD Control", http://buffy.eecs.berkeley.edu/IRO/Summary/98abstracts/xniu.2,html Downloaded from the internet on May 14, 2002. 1 page.

Xinhui Niu, et al, "Specular Spectroscopic Scatterometry in DUV Lithography", Metrology, Inspection and Process Control for Microlithography XII SPIE's 24$^{th}$ Annual International Symposium on Microlithography, SPIE Feb. 1999. Proc. SPIE Int. Soc. Opt. Eng. 3677, 159 (1999). 10 pages.

Joseph C. Pellegrini, "Emerging Trends in Photolithography Analysis and Control", New Vision Systems, Inc., Cambridge, MA., presented at IEEE special Invitation conference, 1996. 8 pages.

Michael Yeung, "Inverse Obstacle Problem in Ellipsometric Scatterometry", one-page summary printed in the Technical Program for PIERS 2002, presented at the Progress In Electromagnetics Research Symposium, Cambridge, MA., Jul. 1, 2002. 1 page.

* cited by examiner

188

METHOD FOR PROCESS OPTIMIZATION AND CONTROL BY COMPARISON BETWEEN 2 OR MORE MEASURED SCATTEROMETRY SIGNALS

CROSS REFERENCE TO RELATED APPLICATIONS

This application claims the priority of the following U.S. patent applications, which are hereby incorporated herein by reference:

Application No. 60/441,048, filed on Jan. 17, 2003 and entitled "METHOD FOR PROCESS OPTIMIZATION AND CONTROL BY COMPARISON BETWEEN 2 OR MORE MEASURED SCATTEROMETRY SIGNALS";

This application is also related to the following U.S. patent applications, which is hereby incorporated herein by reference:

Application Ser. No. 10/186,294, filed on Jun. 26, 2002 and entitled "METHOD FOR DETERMINING LITHOGRAPHIC FOCUS AND EXPOSURE."

Application Ser. No. 10/291,181, filed on Nov. 7, 2002 and entitled "FOCUS MASKING STRUCTURES, FOCUS PATTERNS AND MEASUREMENTS THEREOF."

FIELD OF THE INVENTION

The present invention relates generally to photolithography methods and systems, and more specifically to improved techniques for determining focus and exposure settings of a photolithographic system.

BACKGROUND OF THE INVENTION

Photolithography or optical lithography systems used in the manufacture of integrated circuits have been around for some time. Such systems have proven extremely effective in the precise manufacturing and formation of very small details in the product. In most photolithography systems, a circuit image is written on a substrate by transferring a pattern via a light or radiation beam (e.g., UV or ultraviolet light). For example, the lithography system may include a light or radiation source that projects a circuit image through a reticle and onto a silicon wafer coated with photo resist, i.e., a material sensitive to irradiation. The exposed photo resist typically forms a pattern that after development masks the layers of the wafer during subsequent processing steps, as for example deposition and/or etching.

Two of the most important process parameters for controlling the photolithographic process are focus and exposure. Focus generally deals with clarity with which an optical subsystem of the lithography system renders an image and exposure generally deals with the amount or dosage of light (or radiation) that is used to form the pattern (such as the light produced by a light source of the lithography system). Both affect the circuit pattern in a non-trivial way. For example, changes in focus and exposure may cause changes in the resist profile, i.e., the shape of the circuit printed in the photo resist. The resist profile is often described by three parameters related to a trapezoidal approximation of the profile: the linewidth or critical dimension (CD), the sidewall angle and the height. If the resist profile changes are too great, then the final circuit may not run properly or it may not run at all. By way of example, linewidth is one factor that determines the speed and the timing across the circuit and thus changes thereto may cause one portion of the circuit to run faster or slower than another portion of the circuit (thereby reducing the selling price of the chip since the circuit is clocked to the slower portion). As should be appreciated, the quality of the resist profile is directly related to the quality of the etched or deposited features formed therethrough. In addition, changes to the resist profile may cause open or shorted circuits such that the circuit may need to be discarded or reworked.

Presently, the optimal focus and exposure settings of the lithography system are determined using a focus exposure matrix (FEM), i.e., by exposing a wafer with multiple combinations of focus and exposure, and then inspecting the resultant pattern for the best resist profiles—the resist profiles that more closely match the desired or optimal resist profiles. The inspection is generally performed by a CD scanning electron microscope (CD-SEM) that measures the CD of the resist profile. The focus-exposure matrix may be visualized using a Bossung Plot. The Bossung Plot generally plots CD vs. focus position for varying levels of exposure, i.e., the varying levels of exposure are plotted as contour lines with linewidth representing the Y axis and focus position representing the X axis of the graph. Alternatively, the Bossung Plot may plot exposure vs. focus for varying values of CD, i.e., the values of CD are plotted as contour lines with exposure representing the Y axis and focus position representing the X axis of the graph. Other resist profile parameters, for example, sidewall angle and height may also be visualized using Bossung Plots. These plots are generally harder to obtain since measuring these shapes is often a difficult endeavor. In most cases, the wafer has to be destroyed, i.e., cut through, so that these parameters can be measured. The process window of the system may be determined by plotting multiple resist profile parameters, as for example, linewidth, sidewall angle, and height in the same Bossung Plot. The process window is generally defined as the region of focus and exposure that keeps the final resist profile within prescribed specifications (e.g., process window typically includes the optimum focus and exposure).

Unfortunately, the method described above has several drawbacks. For one, the focus and exposure tests are performed periodically and thus the process may drift out of control between tests. An out of control process may lead to wafers that may need to be scrapped or reworked thus reducing yield and increasing costs. For example, these tests may be performed at 12 hr increments, 1 day increments, 1 week increments and the like. Another drawback is that the lithography system has to stop production in order to perform the tests. That is, the production run must be stopped so that a focus exposure matrix test wafer can be inserted into the system. As should be appreciated, stopping the production run reduces the throughput of the lithography system thereby increasing cycle time and cost.

Attempts to remedy these drawbacks have included using a CD-SEM to measure the CD of a pattern during a production run, and then keeping the CD within prescribed specifications using exposure dose as a manipulated variable to affect changes in CD. Although the focus may have a significant effect on CD, it is assumed in this method that focus is constant and therefore does not effect the CD. Unfortunately, however, the focus of the photolithographic system may (and often does) drift over time making the assumption of constant focus false. Accordingly, this method may not be very accurate since two variables (focus and exposure) may affect the CD rather than one. Furthermore, it should be noted that it is generally not possible to independently manipulate two variables simultaneously (e.g., both focus and exposure) due to the fact that a single measurement type, CD, is the only available test that may be routinely performed, i.e., CD-SEM is typically only capable of measuring CD (e.g., unless using tilted beam CD-SEM). Another method for monitoring focus is generically based on the phenomenon of line end shortening.

In view of the foregoing, improved techniques for determining focus and exposure settings of a photolithographic system are desired. In particular, techniques that allow the system quick feedback by measuring or monitoring production wafers or material so that process drifts may be substantially eliminated without having to stop production.

SUMMARY OF THE INVENTION

The invention relates, in one embodiment, to a process control method. The method includes obtaining scatterometry signals by performing scatterometry measurements on at least two grating structures with different process responses. The at least two gratings structures are located within the same field and in close proximity to one another. The method also includes comparing scatterometry signals from the at least two different grating structures in order to ascertain information about one or more process parameters used to form the at least two grating structures. The method further includes controlling the one or more process parameters based on the comparison. The comparison may include determining the difference between scatterometry signals from the at least two grating structures.

The invention relates, in another embodiment, to a method for controlling one or more process parameters. The method includes obtaining scatterometry signals for at least two grating structures. Each of the grating structures produces a scatterometry signal having different sensitivities to one or more process parameters which are desired to be controlled. The method also includes comparing scatterometry signals in order to ascertain information about one or more process parameters used to form the different grating structures. Each of the scatterometry targets are configured to produce different scatterometry signals. The differences are attributable at least in part to one or more process parameters.

The invention relates, in another embodiment, to a method of determining optimal or best focus. The method includes forming a target group at a plurality of focus settings. The target group containing two or more targets with different sensitivities to focus. The method also includes obtaining scatterometry signals for each of the targets in the target groups. The method further includes calculating difference signals for each target group. The method additionally includes forming a relationship between the difference signal or a property of the difference signal to the focus settings. Moreover, the method includes determining optimal or best focus using the relationship.

The invention relates, in another embodiment, to a process control method. The method includes measuring two or more measurable patterns that are configured to produce different scatterometry signals. The differences between the scatterometry signals being due at least in part to one or more process parameters used to create the measurable patterns. The method also includes analyzing the difference signals to determine the best process conditions for a photolithographic process. The analyzing step includes extracting information about one or more process parameters out of the difference signals.

The invention relates, in another embodiment, to a target group. The target group includes two or more scatterometry targets configured to have different process responses. The two or more scatterometry targets are located within the same field and in close proximity to one another. The scatterometry targets with different process response produce different scatterometry signals. The differences in the scatterometry signals are attributable at least in part to one or more process parameters used to create the scatterometry targets.

BRIEF DESCRIPTION OF THE DRAWINGS

The present invention is illustrated by way of example, and not by way of limitation.

DETAILED DESCRIPTION OF THE INVENTION

Figure 1:
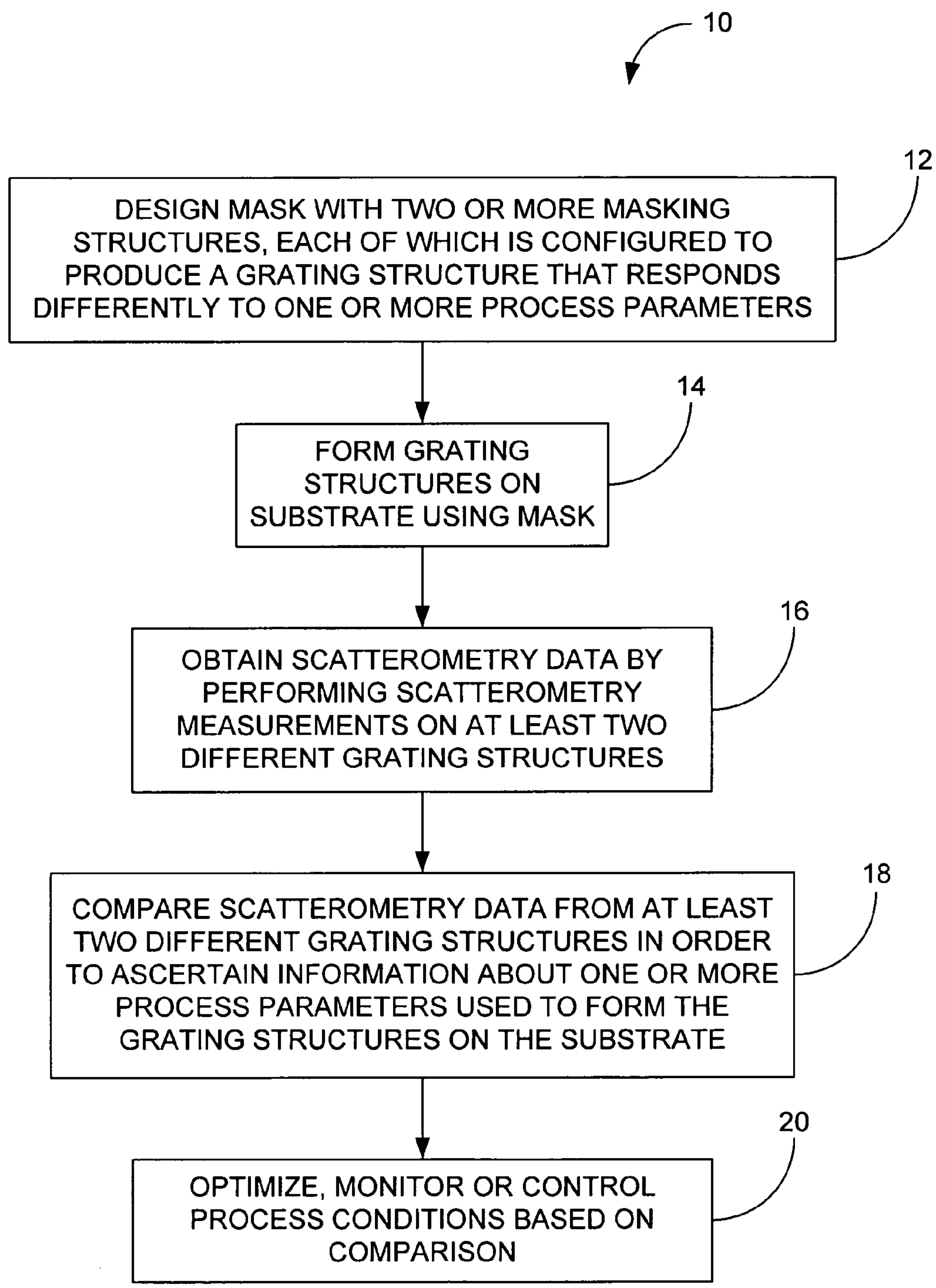
FIG. 1 is a process control method, in accordance with one embodiment of the present invention.

The general objective of the invention is to monitor, optimize and control photolithographic processes using scatterometry measurements and carefully designed measurement sites. The invention generally includes measuring two or more measurable patterns that are configured to produce different scatterometry signals. The differences between the signals are preferably due to one or more process parameters used to create the measurable patterns. The difference signals therefore can be monitored to determine the best process conditions for photolithographic process. For example, information about the process parameters can be extracted out of the difference signals since the differences are based at least partially on the process parameters.

More particularly, the invention includes performing scatterometry measurements on a set of at least two grating structures that have differences that are attributable to one or more process parameters, i.e., when the grating structures were formed they were affected differently by one or more process parameters. The grating structures and the differences therebetween may be produced using carefully designed masks. The differences in the grating structures also show up as differences in the scatterometry spectra for each grating structure, i.e., the different grating structures produce different spectra. Like the patterns, the differences between the scatterometry spectra is also attributable, at least in part, to the one or more process parameters, i.e., the link to process parameters is carried through from the grating structures to the scatterometry spectra. Because the differences are carried through, the scatterometry spectra from each grating structure can be compared to learn information about the process parameters used to create the patterns. This information may be subsequently used to control the process parameters in order to keep the quality of the process within an acceptable level. For example, the difference can be used to trigger an alarm, or it can be used as input to a control mechanism or process control system to determine correction.

In most cases, the different spectra are subtracted from one another in order to produce a difference spectrum or signal. One advantage of subtracting the two scatterometry spectra is that the difference spectrum or signal is somewhat immune to other parameters of the process that effect the two patterns in a similar manner, i.e., the similar conditions cancel out. As a result, the difference is more heavily weighted to the differences in the two patterns and their respective responses to the lithography process parameters rather than other parameters of the process. In general, the desire is to maximize differences caused by the process parameters desired to be monitored while minimizing the differences to other process conditions including for example other process parameters and substrate properties (e.g., film thickness, materials, underlying structures, etc.). That is, the difference spectra changes because of the process parameters desired to be monitored and not something in addition to that.

As is well known, grating structures are defined by several parameters including pitch, linewidth, side wall angle, height, line length, volume, profile and the like. Each of the grating parameters has different sensitivities to the process parameters. Some of the grating parameters are robust to the process parameters and therefore the effects of the process parameters on them are little at best. Other grating parameters are highly sensitive to the process parameters and therefore the effects of the process parameters on them are greater. By way of example, linewidth is sensitive to focus, i.e., changes in focus cause changes in linewidth. When designing the grating structures in the grating structure sets both the robustness and sensitivity of the grating parameters are taken into account.

In the present invention, each of the grating structures in the grating structure set includes at least one sensitive parameter that is deliberately made different therebetween so that the effects of the process parameters on them are different. At least a portion of the remaining grating parameters are made similar so that the effects of the process parameters on them are similar. As a result, the measured scatterometry spectra from each of the grating structures has both similarities and differences. Although not a requirement, it is generally desirable to produce spectra that are weighted to the similarity side rather than the difference side in order to allow for a good comparison between spectra, i.e., some similarity is needed to achieve good comparison sensitive to process differences. Simply put, at least one grating parameter is used to produce similar looking spectra so that the spectra can be easily compared, and another parameter is used to produce differences so that information can be obtained about the process parameters. In one implementation, the pitch of the grating structures is the parameter made similar because pitch is one of the strongest indicators of spectra shape. When the pitch is similar, some differences in the spectra are due to at least in part to the differences found between other parameters such as line width.

When the spectra are subtracted from one another, the similarities are cancelled out thereby leaving the difference. Because the difference is attributable to the process parameters it contains information about the process parameters. As should be appreciated, the difference or some property thereof can be analyzed to determine information about the process parameters. For example, a conversion algorithm, calibration library or calibration curve may be used to convert the difference signal into process parameter information. Conversion algorithms, libraries and curves generally provide predetermined process parameter information related to a given difference signal, i.e., this signal corresponds to a particular process parameter. Furthermore, if more than two grating structures are used in the grating structure sets or if multiple sets of grating structures are used, multiple differences can be obtained and thereafter compared to increase the amount of information about the process parameters. As should be appreciated, a larger number of differences produces more pieces of information about the process parameters.

For example, difference spectras may be obtained between first and second grating structures, between first and third grating structures, and between second and third grating structures, and so on. Different sets of grating structures may also be used to obtain additional difference spectras. Each of these spectras can indicate something about the same process parameter or they can tell you something about different process parameters. By way of example, the first one may be correlated to focus while the second one may correlated to exposure.

In lithography, focus and exposure are two process parameters that have a great impact on patterning of devices and therefore monitoring and controlling focus and exposure is important. Each of these parameters affects the formation of patterns including grating structures in a non trivial way. The grating structures therefore can be specially designed to monitor focus and exposure. The grating structures may for example include different grating parameters that were formed differently because of different sensitivities to focus and/or exposure, i.e., change depending on focus and exposure. By way of example, a first grating structure may include a first parameter having a first value formed from a first sensitivity to focus (and/or exposure) and a second grating structure may include a first parameter having a second value formed from a second sensitivity to focus (and/or exposure). The second sensitivity may be greater or less than the first sensitivity to focus (and/or exposure). This example set may include additional grating structures, which have different sensitivities to focus (and/or exposure) in order to obtain more pieces of information about focus (and/or exposure). Additional sets of grating structure sets may also be used to obtain even more information. For example, a second set of grating structures more sensitive to the other process parameters such as exposure may be used. In one particular embodiment, focus is monitored with grating structures having different line widths that were affected differently by the sign and magnitude of focus. As mentioned above, linewidth is one parameter that is highly sensitive to focus.

Embodiments of the invention are discussed below with reference to FIGS. 1-13. However, those skilled in the art will readily appreciate that the detailed description given herein with respect to these figures is for explanatory purposes as the invention extends beyond these limited embodiments.

FIG. 1 is a process control method 10, in accordance with one embodiment of the present invention. The process control method is generally configured to ascertain information about one or more process parameters, which were used to form a pattern on a substrate during a photolithographic process. The information may be used to improve the control of subsequent lithographic patterning and to determine whether the quality of the photolithographic pattern meets specified requirements. As should be appreciated, process parameters generally refer to parameters used to control the processing conditions of the lithography system. By way of example, process parameters may correspond to focus offset, exposure dose, resist thickness, develop time and temperature, post exposure bake time and temperature and the like.

The process control method generally begins at block 12 where a mask is designed. The mask is generally provided to produce a measurable pattern that includes information about one or more process parameters used to form the measurable pattern. The process information can be extracted out of the measurable pattern in order to ascertain the quality of the patterning step or patterning system. The mask may be a test mask used for testing or calibration or a production mask for forming circuit patterns on a wafer. In the simplest case, the mask is designed with two or more masking structures, each of which is configured to produce a corresponding grating structure with a different process response. By different process response, it is generally meant that each of the grating structures responds differently to one or more "selected" process parameters. By selected, it is generally meant that these process parameters are selected out of a number of process parameters. The selected process parameters are typically the process parameters desired to be optimized, monitored or controlled. By way of example, the selected parameter may correspond to focus and/or exposure.

In one embodiment, the scatterometry target masking structures produce grating structures with corresponding or related parameters that have different sensitivities to the selected process parameters (and thus different process responses). That is, the scatterometry target masking structures create grating structures on the wafer or substrate with corresponding parameters that change in accordance with the value of the selected process parameters. The sensitivities may be obtained by careful selection of sensitive parameters or by utilizing assist features that produce different sensitivities. The parameters may for example include linewidth, height, sidewall angle, length, feature volume, profile. As should be appreciated, each of these may have a different response to a particular process parameter. By way of example, line width is very sensitive to focus and thus it may be utilized to obtain information about focus as for example the sign and magnitude of focus. The assist features, on the other hand, may include scattering bars, serifs, cut-ins and the like.

Following block 12, the process flow proceeds to block 14 where the grating structures with different process responses are formed on a substrate. The grating structures are formed using a set of process parameters such as focus and exposure. In general, the grating structures are printed on the surface of a work piece when light is made to travel through their corresponding masking structures (which are designed to produce different process responses). By way of example, the surface may represent an exposed layer of photo resist, a partially developed layer of photo resist, a developed layer of photo resist, an underlying layer of the wafer (e.g., etched into metal or dielectric) and/or the like. As is generally well known, light or radiation induces chemical and physical changes in the photo resist that can be developed into a structural pattern.

The grating structures are configured to produce similar but different scatterometry signals, the differences are preferably attributable to one or more process parameters used to create the grating structures. The parameters of the grating structures that changes differently relative to one another is generally chosen based on its sensitivity to one or more process parameters.

The grating structures may be printed on a test wafer as a part of a test procedure or they may be printed on a production wafer during production. During tests, the grating structures may be printed across the entire test wafer. In production, the related gratings structures are typically positioned in the scribe line between device structures (e.g., dies that define the IC). Additionally or alternatively, they may be located within the device structures themselves. The grating structure may in fact be a portion of the device structure. In one embodiment, the related grating structures are all positioned in the scribe line. In another embodiment, at least one of the related grating structures is positioned in the device structure and another one of the grating structures is positioned in the scribe line. In yet another embodiment, the related grating structures are all positioned within the device structure.

The related grating structures are preferably formed in the same field and in close proximity to one another so as to minimize differences to properties other than the properties desired to be controlled so that they are formed with the same process conditions, from the same films, from the same underlying structures, same materials, etc. This is sometimes referred to as common mode. In general, it is desirable to have all properties other than the properties that you are trying to control to be common mode. As should be appreciated, process parameters, underlying films, surface materials, etc. can vary across the wafer and within the field.

In some cases, the gratings structures are periodic structures formed by parallel printed lines that change differently in accordance process parameters used to form them. Because they change in accordance with the process parameters, they contain information about the process parameters. This information can be extracted out in later steps in order to optimize, monitor or control the process parameter. The lines may be governed by parameters such as pitch, line width, side wall angle, height, pitch, top-profile (degree of top rounding or T topping), bottom profile (footing) and the like.

The grating structures may be periodic in one direction (X or Y) as for example a line grating, or it may be periodic in two directions (X and Y), as for example a grid grating. Alternatively, the grating may be periodic in a direction not aligned to the X or Y axes, but may be periodic along one or more directions at angles to the X and Y axes, for example at 45 degrees to the X axis.

The number of grating structures within a grating structure set as well as the number of grating structures sets may be widely varied. It is generally believed that the greater number, the greater the information that can be used to determine the process conditions. However, there is typically a trade off between available space, desired measurement time and more information. The desirable amount is typically defined as the minimum number of grating structures that will do the job, i.e., provide the necessary information to optimize, monitor or control the selected process parameters.

In one embodiment, one target (or grating structure) is constructed as a periodic array of device structures with the same pitch, layout and critical dimensions as the device. This target may actually be measurement area in the device or a measurement target specifically designed for measurements. A second target (or grating structure) is designed with the same periodic structure and layout, but with a different line width for the most critical device feature. If for example, the critical device feature is an isolated, narrow line, then the second target could be designed to be the same as the first measurement target except for making the line width of the critical feature wider. The wider line should be less sensitive to focus than the narrower line, especially if the narrow line is near the limit of the lithography process capability. The best focus conditions for the device may be taken as when the width, (or area or volume) of the narrow device line segments are maximum which will be seen as when the difference between the spectral from the first and second targets in minimum.

It should be noted that using two targets is not a limitation and that more than two targets may be used. By way of example, second and third targets could be designed with the same pitch but with larger and smaller line widths than the first target that corresponds to the device structure. The best focus should correspond the minimum difference in spectra between the targets.

In another embodiment, one target (or grating structure) is constructed as a periodic array of contact holes with the same pitch, layout and critical dimensions as the device. This target may actually be a measurement area in the device or a measurement target specifically designed for measurements. A second target (or grating structure) is designed with the same periodic structure and layout, but with a different critical dimension chosen such that the scatterometry signal will be more or less sensitive to the process parameter you are trying to control. For example, the diameter of the contacts of the second target may be larger than the first target, giving the second target less sensitivity to focus than the first target. The best focus conditions for the device are when the diameter (or area or volume) of the device contacts are maximum which will be seen as when the difference between the spectra from the first and second targets is minimum.

In another embodiment, one target (or grating structure) is constructed as a periodic array of line segments with the same pitch, layout and critical dimensions and optical proximity correction (OPC) as the device. This target may actually be measurement area in the device or a measurement target specifically designed for measurements. A second target (or grating structure) is designed with the same periodic structure and layout, but with a different OPC or no OPC chosen such that the scatterometry signal will be more sensitive to the process parameter you are trying to control. For example, the line end shortening (and line end angle) of the uncorrected line segments without OPC on the second target will be larger than the first measurement target, giving the second measurement target more sensitivity to focus than the first target. The best focus conditions for the device may be taken as when the dimension, (length, or 2D, top-down area, or 3-D volume) of the uncorrected line segments are maximum. This condition may be indicated when the difference between the spectra from the first and second targets is minimum.

Following block 14, the process flow proceeds to block 16 where scatterometry signals are obtained by performing scatterometry measurements on at least two different but related grating structures. The related grating structures are deemed different because they each have different process responses, i.e., they each responded differently to one or more process parameters. Because the grating structures have different process responses, the scatterometry signals produced therefrom are also different. These differences are preferably due to one or more of the process parameters used to create the different grating structures. The grating structures are chosen such that the resulting scatterometry signal is either more or less sensitive to the selected process parameter.

In scatterometry, one or more light or radiation beams are made incident on a grating structure and some or all of the scattered, reflected and/or diffracted beams scattering from the grating structure are measured. The incident light may be directed toward the pattern normally or at some angle to the normal. The light scattering from the grating structure is typically scattered, reflected and/or diffracted at various orders, i.e., angles relative to the incident light. The characteristics of the scattered, reflected and/or diffracted light (e.g., intensity, phase, polarization, and the like) from at least some of the various orders is measured thereby forming a measurement signal or measured spectra.

The scattering, reflecting and diffracting of light, and therefore the measured spectra is generally dependent on the many factors including but not limited to: the line widths, line spacings, the pitch, the optical properties (n(lambda), k(lambda), the shapes and profiles (e.g., critical dimensions), height, sidewall angle, sidewall roughness, T-toppings, footing, features, volume, etc. Because these are typically the parameters that are affected by the process parameters, the measured spectra generally reveals information about the process parameters used to create the grating structures. That is, the scattered, reflected and/or diffracted light is different for different grating structures and thus the scattered, reflected and/or diffracted light may be used to ascertain information about the process parameters, i.e., there is a unique relationship between the measured spectra and the profile of the grating structure.

The scatterometry technique used to measure the grating structure (e.g., periodic) may be widely varied. For example, reflectometry, spectroscopic ellipsometry, spectroscopic reflectometry, multiwavelength reflectometry, polarized spectroscopic reflectometry, multiangle multiwavelength reflectometry or angle resolved scatterometry may be used. Further, the measurement may be performed in a fixed angle spectroscopic ellipsometry mode, in an angle scanning single or multiple wavelength mode, or in a multiple angle multiple wavelength mode. That is, the beam(s) may be brought in at a single or multiple angles and they may be brought in at a single wavelength or at multiple wavelengths. In addition, the beams may be detected at a single angle or multiple angles and they may be detected at single or multiple wavelengths. Furthermore, the intensity, polarization and/or optical phase of the beams may be measured at different angles and/or different wavelengths.

Following block 16, the process flow proceeds to block 18 where the different scatterometry signals are compared in order to ascertain information about one or more parameters used to form the grating structures on the substrate. In one embodiment, the different scatterometry signals are subtracted from one another in order to produce a difference (portions of or the entire signal). The difference may be in the form of a signal, spectra or value that is representative of the difference. The difference because of the aforementioned reasons includes information about the selected process parameters. By subtracting, the similarities of the spectra from the grating structures are cancelled out leaving only the differences therebetween. The difference in the signal are attributable to one or more process parameters. For example, information contained in the spectra concerning materials or underlying structures are largely cancelled out.

Following block 18, the process flow proceeds to block 20 where the process conditions are optimized, monitored or controlled based on the comparison. In one embodiment, the difference signal is compared to calibration data in order to determine the effective value of the selected process parameters. The calibration data may for example include difference signals that have been calibrated to one or more process parameters. In one implementation, the calibration data comes in the form of one or more equations (difference signal(s) as a function of one or more process parameters). In another implementation, the calibration data comes in the form of graphical plots representative of the functions. In yet other implementations, the calibration data comes in the form of a library. For example, the difference signal is compared to a plurality of difference signals that were previously calibrated to process conditions until a match is found.

The estimated or predicted values of the process parameters determined may be used to control subsequent processing to keep the process within desired limits. For example, the effective values of the process parameters compared with the nominal values to produce a process parameter correction. The correction may be used to help control the lithographic process (by adjusting the process parameters). These corrections may be produced in a die to die mode, a wafer to wafer mode, a lot to lot mode, other feed back control system and the like.

In another embodiment, the difference is controlled using control limits or threshold values. For example, the process parameters are maintained within predetermined control limits. If the difference goes outside of the predetermined control limits then the system may be placed in alarm status so that an adjustment can be made to correct the out of control process. One example of a process control methodology is statistical process control.

In one particular embodiment of FIG. 1, the scatterometry signals are measured with a spectroscopic ellipsometer as for example the KLA-Tencor ASET F5 manufactured by KLA Tencor or San Jose, Calif. The signals are saved to a memory device such as memory on a microprocessor, computer RAM, or a magnetic or optical disk drive. The signals are compared in a computer program (or electronically including digital or analog electronics). The difference signal between spectra from the grating structures is compared to a calibration curve, calibration formula or calibration library to determine the process parameters used to create the grating structures. The calibration may be determined empirically by measuring several sets of grating structures with known process parameters, calculating the difference signal between the pair of grating structures versus the known process parameters, and storing the resulting calibration values derived from the calibration data. The known errors may be a nominal parameter value or it may be measured with reference measurement system capable of measuring the process parameter(s).

In one embodiment, the method described in FIG. 1 is used to control, monitor or optimize a single process parameter such as focus or exposure. In another embodiment, the method described in FIG. 1 is used to control, monitor or optimize multiple process parameters such as focus and exposure.

Figure 2A:
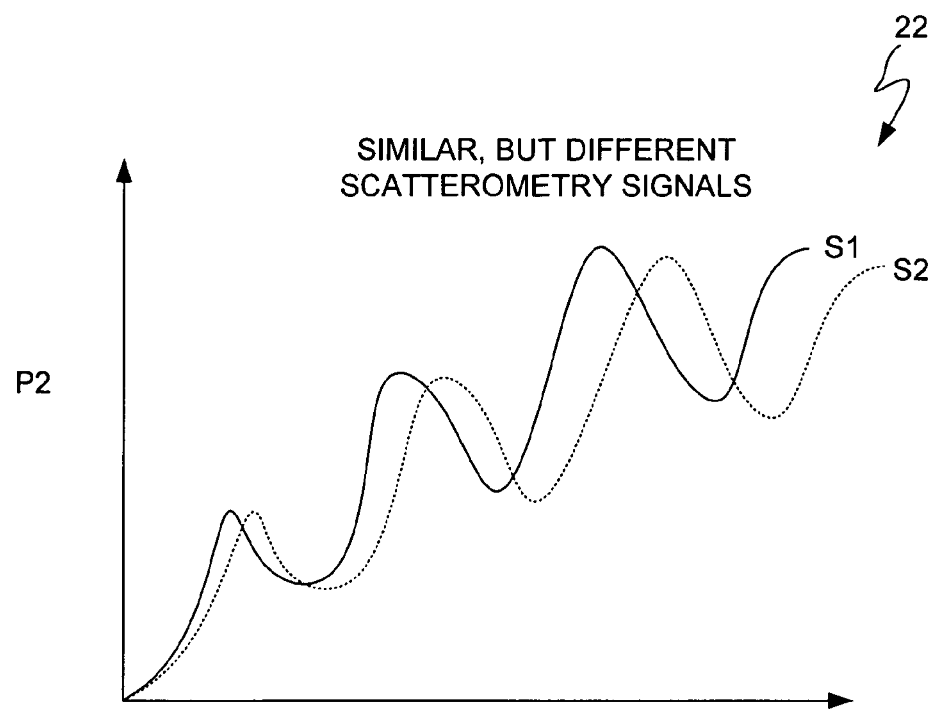
FIG. 2A is a diagram of a pair of scatterometry signals, in accordance with one embodiment of the present invention.

FIG. 2A is a diagram of a pair of scatterometry signals S1 and S2, in accordance with one embodiment of the present invention. The scatterometry signals S1 and S2 may for example be produced by measuring a set of gratings structures with different process responses. Each of the scatterometry signals (or spectra) is a collection of information over different optical conditions. As shown, the scatterometry signals have a similar but different shape. The signals are similar, but shifted due to programmed differences in the two scatterometry signals. The scatterometry signals can be widely varied. The scatterometry signals are generally plotted as one scatterometry parameter P2 (y axis) verses another scatterometry parameter P1 (x axis). The first scatterometry parameter P2 may for example correspond to SE, $\alpha$, $\beta$, tan $\psi$, cos, R or the like while the measurement parameters P1 may correspond to wavelength, angle of incidence, or polarization angles.

Figure 2B:
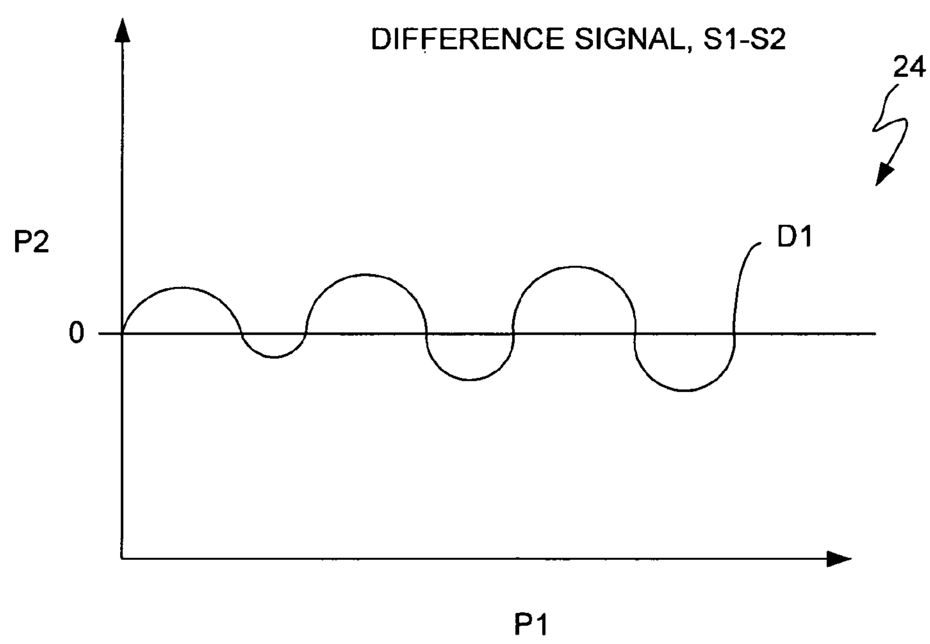
FIG. 2B is a diagram of a difference signal, in accordance with one embodiment of the present invention.

FIG. 2B is a diagram of a difference signal D1, in accordance with one embodiment of the present invention. The difference signal D1 may for example be produced by subtracting the scatterometry signals S1 and S2 of FIG. 2A. Although only one difference signal is shown, it should be noted that multiple difference signals may be obtained and plotted together. Each of the difference signals can be formed from different sets of grating structures.

Figure 3:
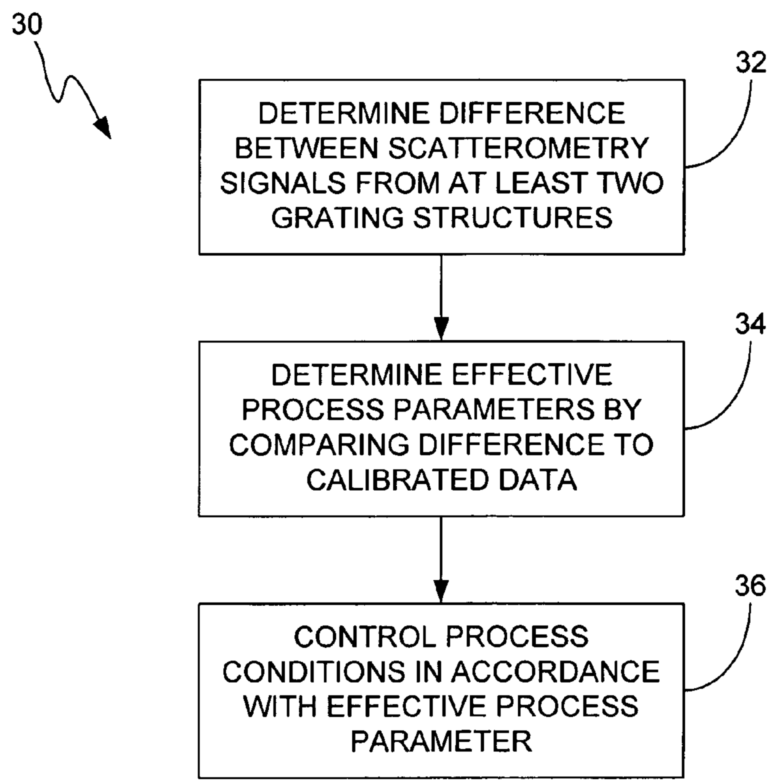
FIG. 3 is a processing control method, in accordance with one embodiment of the invention.

FIG. 3 is a processing control method 30, in accordance with one embodiment of the invention. The processing control method 30 may for example generally correspond to blocks 16 and 18 shown in FIG. 1. The processing control method 30 generally begins at block 32 where differences between two different scatterometry signals are determined. The difference may be found between the entire scatterometry signals or between a portion of the scatterometry signals. The difference is generally determined by subtracting the two scatterometry signals.

Following block 32, the process flow proceeds to block 34 where one or more effective values of one or more process parameters are determined by comparing the difference to calibration data. For example, the process parameters may be extracted from the difference spectra by utilizing an equation, graph or library that relates hundreds of thousands of difference spectra to hundreds of thousands of process parameter settings.

Following block 34, the process flow proceeds to block 36 where the process conditions are controlled in accordance with the effective values of the process parameters. In one embodiment, the effective values are used to form a correction. For example, the effective values are compared with the nominal values of the process parameters. Any difference therebetween can be accounted for by adjusting the process parameters. The correction may be inputted into the lithography system in order to maintain the process (e.g., automated process control).

The calibration data in block 34 may be produced using a variety of techniques. For example, the calibration data may be produced using simulation methods or empirical methods. For example, the calibration data may be produced using simulation methods including lithographic simulation methods combined with scatterometry simulation methods. Lithographic simulation methods generally produce calibration data by performing calculations to obtain the shapes of the grating structures as a function of lithographic process parameters. In most cases, the lithography and resist processing simulations are calibrated such that the calculated shapes accurately correspond to the grating shapes obtained on a real wafer. One example of a lithography simulation program that can be used to calculate the grating element shapes for varying lithography parameters is PROLITH manufactured by KLA-Tencor of San Jose, Calif. The simulated grating element shapes can be used as inputs into a scatterometry simulation program to produce simulated scatterometry spectra that corresponds to the simulated grating element shapes and the corresponding lithography process parameters used in the simulation.

The empirical lithographic measurement methods, on the other hand, generally produce calibration data by printing a plurality of grating structures on one or more test wafers using various process parameters, determining the difference for sets of the grating structures, and correlating the difference with the various process parameters. As already mentioned, the grating structures are typically dependent on the process parameters and thus changes in the process parameters cause changes in the grating structures. In addition, the spectra are dependent on the grating structures and thus changes in grating structures cause changes in spectra. Moreover, the spectra difference is dependent on the spectra and thus changes in spectra cause changes in the spectra difference. The differences may be characterized over a wide range of values thereby forming libraries, equations or graphical plots that describe the impact of these parameters on each other.

To elaborate, printing is generally accomplished in a layer of photo resist by projecting light or radiation through a pattern of a reticle. The structures are normally printed across the entire test wafer using a different combination of process parameters (test matrix). That is, each structure may be printed with different process parameter levels. For example, the structures may be printed with varying levels of exposure and focus—for different exposure fields across the wafer, vary focus in one direction and exposure in the other direction so as to produce a matrix of different values of exposure and focus across the wafer (e.g., focus-exposure test matrix). When using multiple test wafers, the same or different test reticles may be used. The different test reticles may have grating structures with different dimensions so as to produce a wider range of test data. As should be appreciated, different dimensions may produce different spectra and thus different differences for the same processing conditions.

Figure 4:
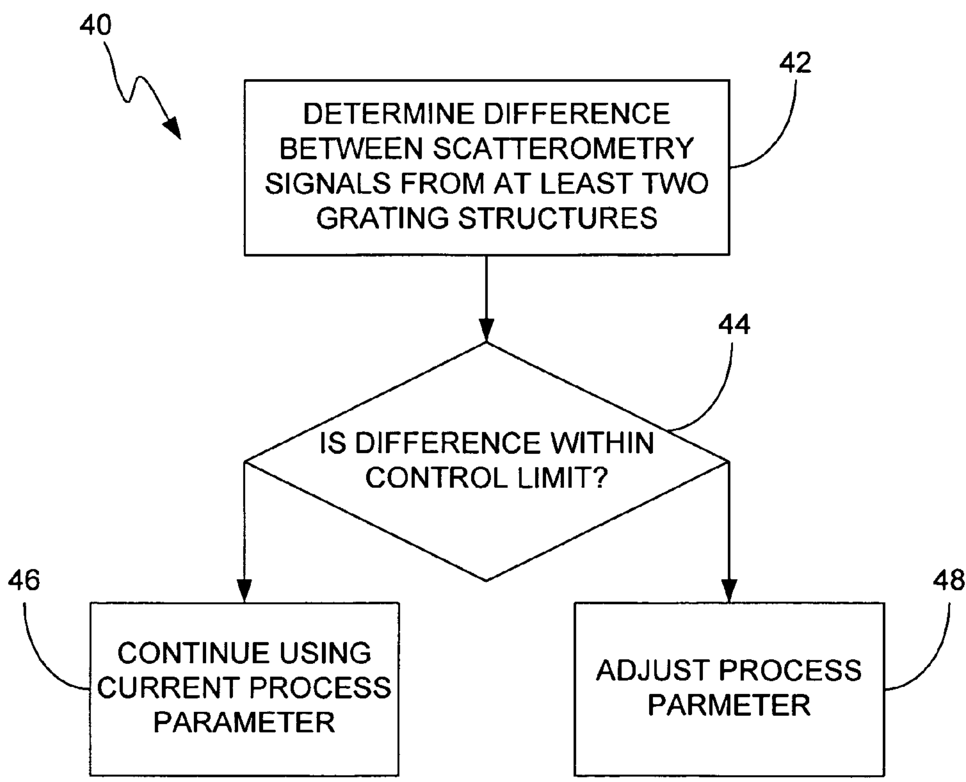
FIG. 4 is a processing control method, in accordance with one embodiment of the invention.

FIG. 4 is a processing control method 40, in accordance with one embodiment of the invention. The processing control method 40 may for example generally correspond to blocks 16 and 18 shown in FIG. 1. The process control method may for example be configured to maintain the best process conditions by controlling the process parameter to keep the difference between scatterometry signals for the two grating structures within a certain range. Processing control method 40 generally begins at block 42 where differences between two different scatterometry signals are determined. The difference may be found between the entire scatterometry signals or between a portion of the scatterometry signals. The difference is generally determined by subtracting the two scatterometry signals.

Following block 42, the process flow proceeds to block 44 where a determination is made as to whether or not the difference is within a predetermined control limit. The predetermined control limit may have been established in previous test steps or from historical production data as in statistical process control.

If the difference is within the predetermined control limit then the process flow proceeds to block 46 where the values of the current process parameters are used during subsequent processing. If the difference is outside the predetermined control limit then the process flow proceeds to block 48 where the values of the process parameters are adjusted in accordance with control limits. For example, the values of the process parameters may be increase or decreased based on the proximity of the difference to the established upper and lower control limits.

An optional step may be included between blocks 44 and 48. The optional step may include alarming or stopping the process when the difference is outside the control limit. The optional step may additionally include determining a necessary correction based on how far outside the difference is relative to the control limits. The correction step may include performing a conventional test matrix associated with the process parameter desired to be controlled.

Figure 5:
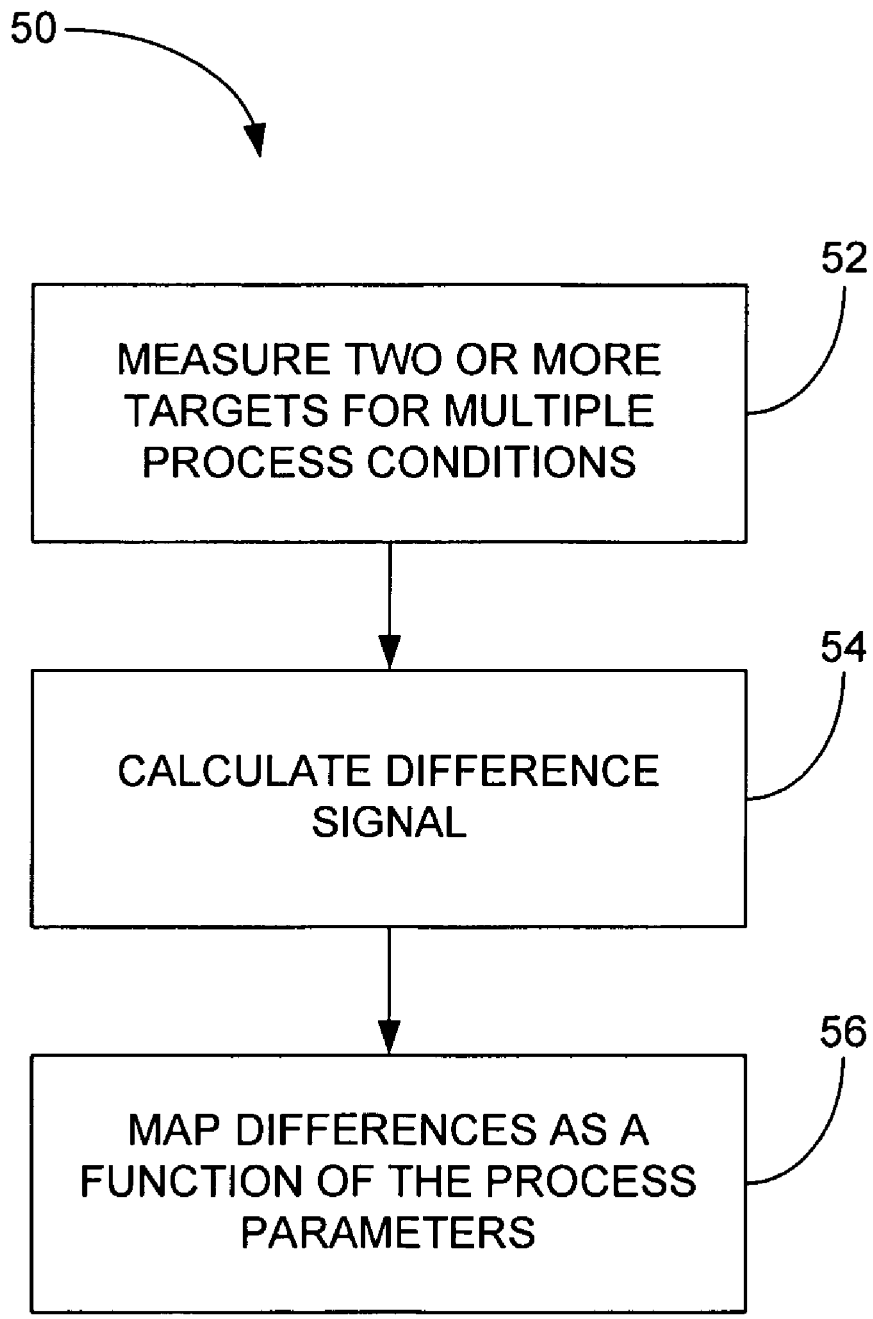
FIG. 5 is a calibration method, in accordance with one embodiment of the present invention.

FIG. 5 is a calibration method 50, in accordance with one embodiment of the present invention. The calibration method may for example be used to establish the calibration data that is used in block 34 of FIG. 3. The calibration method 50 generally begins at block 52 where a plurality of sets of two or more grating structures with different process responses are measured for varying process conditions. The measurements are configured to produce data representative of each grating structure in the grating structure sets. The measurements may be performed on a test matrix such as a focus exposure matrix.

Following block 52, the process flow proceeds to block 54 where differences between spectra are calculated. The differences are found between at least two of the grating structures in the grating structure sets.

Following block 54, the process flow proceeds to block 56 where one or more differences are mapped as a function of the process parameters. For example, a library, equation, a graph associating the differences to the appropriate process parameters used to form the differences may be produced. By way of example, the libraries, graphs and equations may correlate difference verses focus, difference verses exposure, or difference verses focus and exposure. An optional step may be included between blocks 54 and 56. The optional step may include obtaining one or more properties of the difference. For example, the root mean square difference of the difference signal may be calculated (RMSD).

In one embodiment, the calibration method utilizes a focus exposure matrix: In this methodology, at least two grating structures in close proximity and with different process responses is made repeatedly for differing levels of focus and exposure, the grating structures are measured using scatterometry to produce different spectra for each of the grating structures and thereafter a difference between the spectra associated with the grating structures are calculated. By way of example, 10 focus steps and 10 exposure steps may performed across the wafer in order to produce 100 process conditions.

Figure 6:
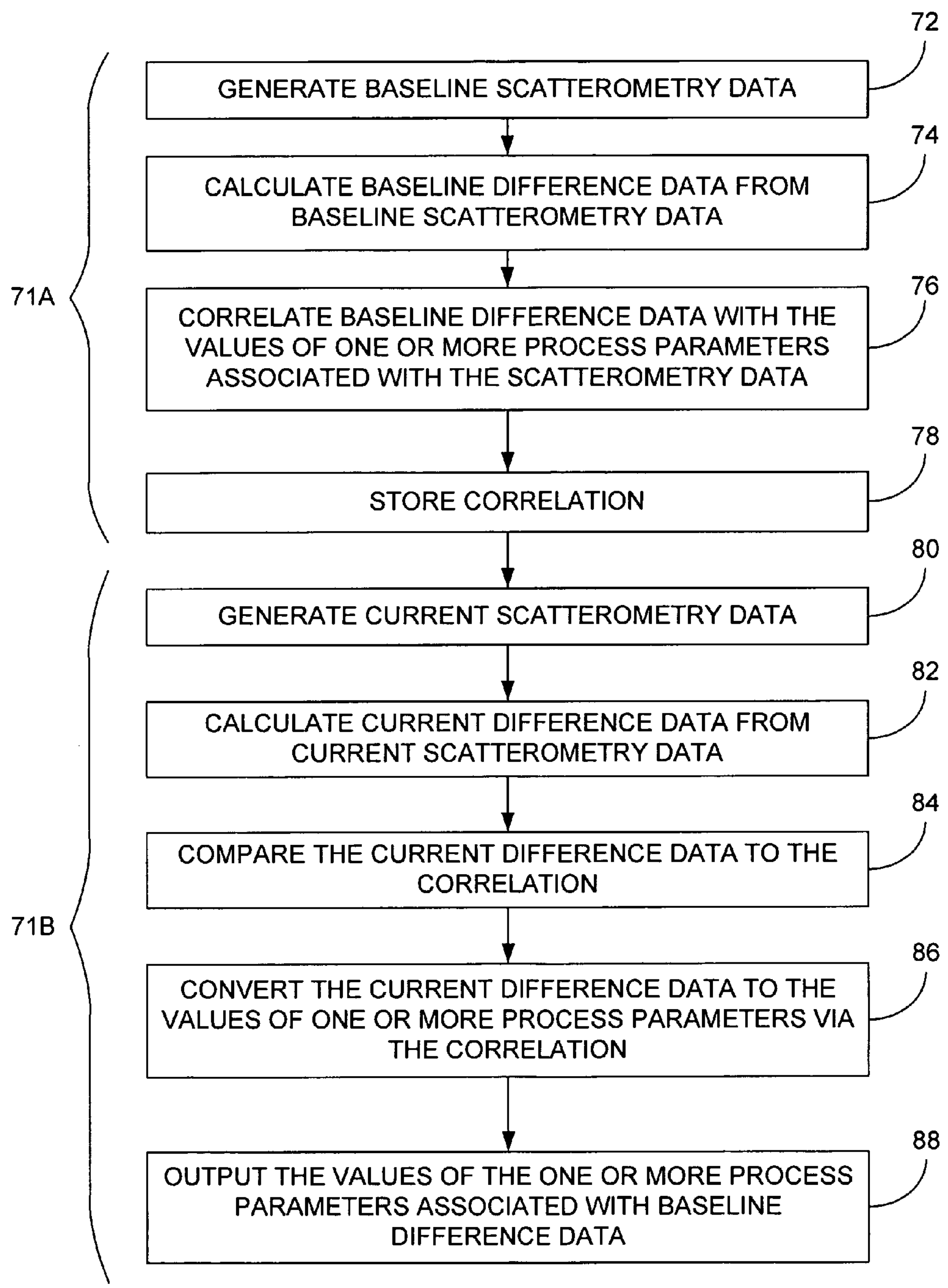
FIG. 6 is a process control method, in accordance with one embodiment of the present invention.

FIG. 6 is a process control method 70, in accordance with one embodiment of the present invention. The method 70 is generally performed in multiple steps including a calibration step 71*a* and a production step 71*b*. The calibration step 71*a* is performed before the production step 71*b*. The calibration step 71*a* is generally performed once while the production step 71*b* is performed incrementally during production.

The calibration step 71*a* generally begins at block 72 where baseline scatterometry data is generated. This may for example be accomplished by measuring sets of gratings structures for varying process conditions. The scatterometry data includes signals or spectra associated with each of the grating structures.

Following block 72, the process flow proceeds to block 74 where baseline difference data is calculated from the baseline scatterometry data. This may for example be accomplished by subtracting signals or spectra associated with grating structure sets. The difference data includes difference signals associated with each grating structure set.

Following block 74, the process flow proceeds to block 76 where the difference data is correlated with the values of one or more process parameters. By correlating, it is generally meant that a relationship is made between the difference signals associated with each grating structure set and one or more process parameters associated with each grating structure set. The relationship may be characterized over a wide range of values.

In one embodiment, the correlation includes one or more differences as a function of one or more process parameters (e.g., differences are dependent on process parameters). For example, the correlation may include a single difference as a function of a single process parameter, a single difference as a function of more than one process parameter, a plurality of differences as a function of a single process parameter or a plurality of difference s as a function of a plurality of process parameter.

Following block 76, the process flow proceeds to block 78 where the correlation of baseline difference data and process parameters is stored. The correlation may for example be stored in a database.

The production step 71*b* generally begins at block 80 where current scatterometry data is generated. This may for example be accomplished by measuring one or more sets of gratings structures for current process condition settings. The scatterometry data includes signals or spectra associated with each of the grating structures of the grating structure sets.

Following block 80, the process flow proceeds to block 82 where current difference data is calculated from the current scatterometry data. This may for example be accomplished by subtracting signals or spectra associated with grating structure sets. The difference data includes difference signals associated with each grating structure set.

Following block 82, the process flow proceeds to blocks 84 where the current difference data is compared to baseline difference data that has been correlated to one or more process parameters.

Thereafter, the process flow proceeds to block 86 where the values of one or more process parameters associated with forming the grating structures are determined based on the comparison. This may be accomplished via one or more equations, graphical plots or libraries representative of the correlation. By way of example, conversion calculations or graphical comparisons using the functions obtained in the calibration mode and the measurements obtained in the production mode are performed. When using libraries, the current difference data may be matched to similar baseline difference data and the corresponding process parameters that produced the matched baseline difference data is selected as the process parameters that formed the gratings structures.

Following block 86, the process flow proceeds to block 88 where the values of the process parameters associated with the baseline difference data are outputted. The outputted values may be used in a process control system either automatically (e.g., an automated process control system determines the required corrections and the litho tool makes adjustments based on the outputted process parameters) or manually (e.g., the value is outputted and an operator makes the adjustment decision). Alternatively, the outputted process parameters values may be used to trigger an alarm, which indicates that the process is out of control.

In one embodiment, the measurements are performed with a scatterometry measurement tool capable of measuring grating structures. The measurement tool may be an in situ or ex situ measurement tool. That is, the measurement tool may be integrated with the lithography tool or it may be a stand alone device. With regards to the integrated measurement tool, the measurement tool may cooperate with the lithography process tool to change process parameters in real time or while the wafer is still in the lithography tool. That is, the measurement tool may provide a feedback control signal to the lithography tool so as to correct the process parameters. By way of example, the control signal may be used to control some aspect of the optics and/or wafer to achieve and maintain the best possible focus. For example, the position of the optics and/or the wafer may be adjusted so that the ideal focus plane substantially coincides with the surface of the wafer. Alternatively, the focus information may be displayed to an operator so that the operator may make adjustments.

Figure 7:
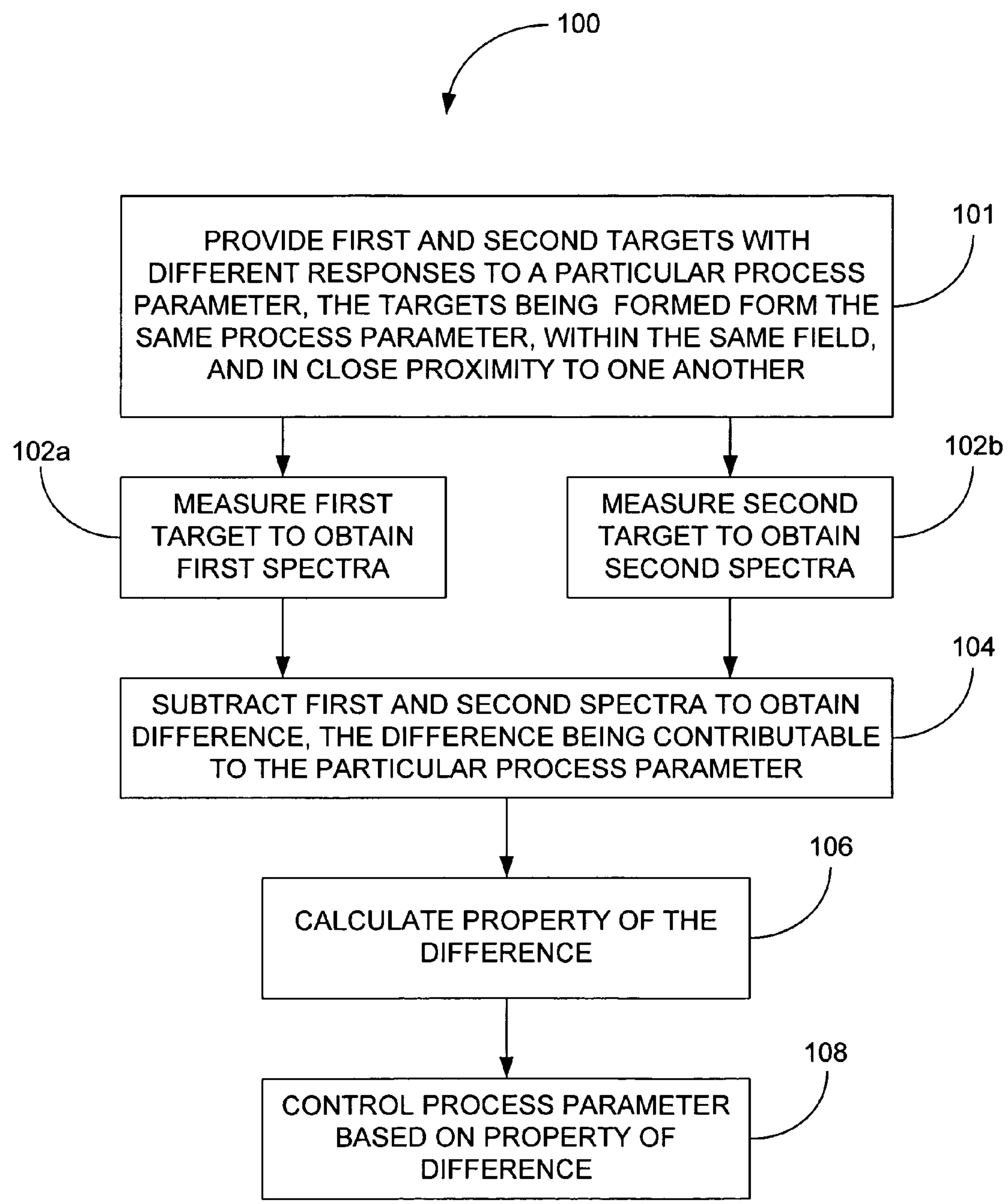
FIG. 7 is a flow diagram illustrating a procedure for controlling a process, in accordance with one embodiment of the present invention.

FIG. 7 is a flow diagram illustrating a procedure 100 for controlling a process, in accordance with one embodiment of the present invention. In this embodiment, first and second targets with different responses to a particular process parameter are provided in operation 101. The targets, which are located within the same field and in close proximity to one another, are formed from the same process parameter. Because they are located within the same field and in close proximity to one another they have the same characteristics, such as film characteristics, structure size and composition. Both of the targets may for example be located in the scribeline between devices, in the device structure it self or in both the scribeline and the device structure. When located within the device the target may be a portion of the device.

One example of scatterometry targets are periodic grating structures that consist of two or more parallel lines. At least one of the grating parameters of the grating structures was altered in a different manner by the particular process parameter, i.e., they each had different sensitivities to the particular process parameter. The remainder of the grating parameters are common mode, they are the same for both targets. By way of example, the common grating parameters may include pitch, materials, underlying materials and the like.

In one particular embodiment, the targets are formed with the same pitch and different linewidths. For example, the first target includes a nominal linewidth, which is strongly correlated to the dimension of the device, and the second target includes a linewidth that is thinner or thicker than the nominal linewidth. As should be appreciated, thinner linewidths have a greater sensitivity to focus while thicker linewidths have a lower sensitivity to focus.

Figure 9:
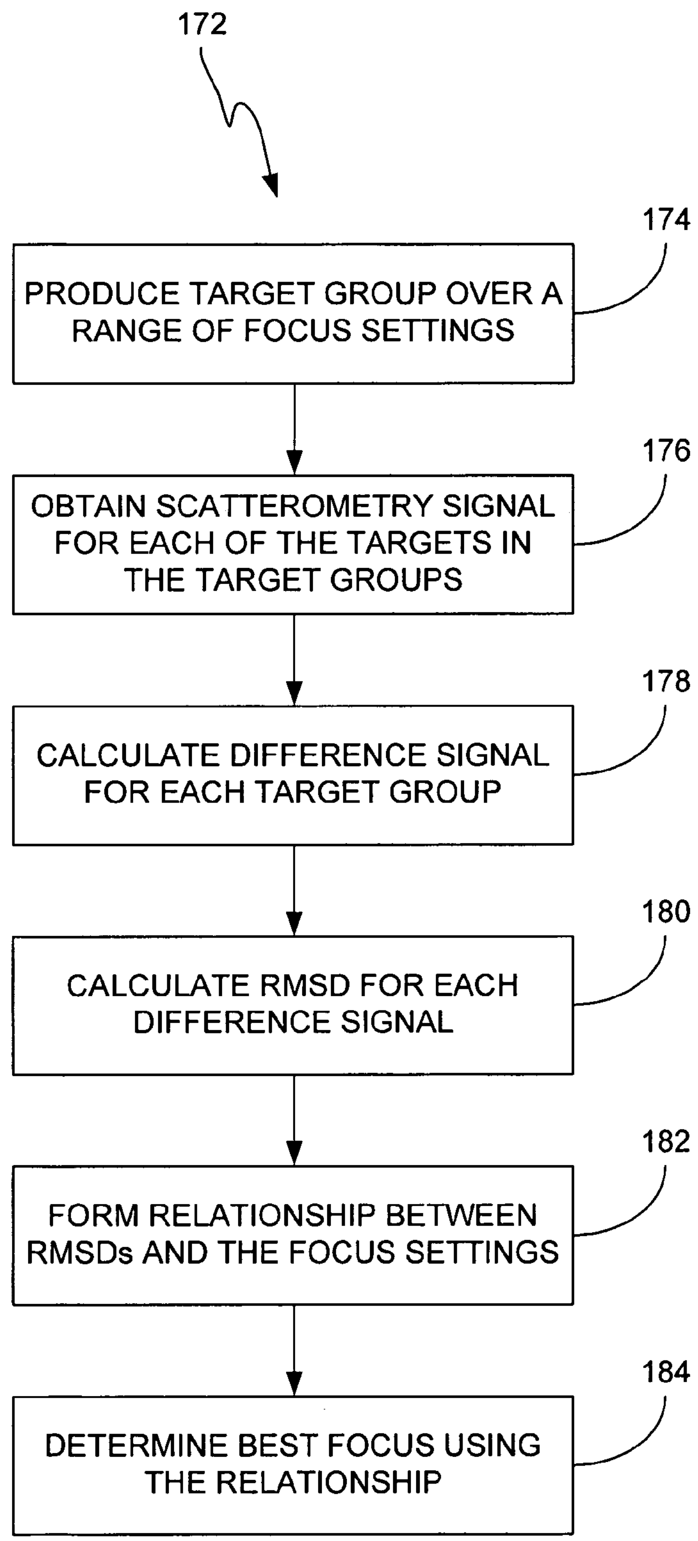
FIG. 9 is a method of determining optimal or best focus 172, in accordance with one embodiment of the present invention.

In operations 102*a* and 102*b*, an incident radiation beam is directed towards the first and second targets A and B to measure first and second spectra $S_A$ and $S_B$. Examples of first and second spectra are shown in FIG. 2A. Operations 102*a* through 102*b* may be carried out (in series or parallel) sequentially or simultaneously depending on the measurement system's capabilities. The incident beam may be any suitable form of electromagnetic radiation, such as laser or broadband radiation. The spectra $S_A$ and $S_B$ may include any type of spectroscopic ellipsometry or reflectometry signals, including: tan(Ψ), cos(Δ), Rs, Rp, R, α (spectroscopic ellipsometry "alpha" signal), β (spectroscopic ellipsometry "beta" signal),((Rs−Rp)/(Rs+Rp)), etc. Examples of an optical system for measuring scatterometry signals is shown in FIG. 9.

In operation 104, spectra $S_B$ is subtracted from spectra $S_A$ to form difference spectra D, respectively. An example of difference spectra is shown in FIG. 2B.

Next, a difference spectra property P is obtained from the difference spectra D in operation 106. The difference spectra property P is generally obtained from any suitable characteristic of the obtained difference spectra D. The difference spectra property P may also simply be a point on the difference spectra D at a particular wavelength. By way of other examples, difference spectra property P may be the result of RMSE (root mean square error), RMSD (root mean square difference), chi2 (weighted by noise at each wavelength, angle of incidence, etc), average difference, difference at one wavelength, integrated difference over a range of wavelengths, weighted by process parameter sensitivity, an integration of averaging of the difference signal, equal an average of the SE alpha signal, equal a weighted average (which accounts for instrument sensitivity, noise or signal sensitivity to the process parameters), a squared difference signal, an average squared difference signal, and the like.

After the difference spectra property P is obtained, the process parameters may be controlled based on the property of the difference as shown in operation 108. In one embodiment, the process parameter is calculated directly from the difference spectra property P. In another embodiment, the process parameter is determined by comparing the difference property to previously calibrated data that contains difference properties as a function of process parameters.

Figure 8:
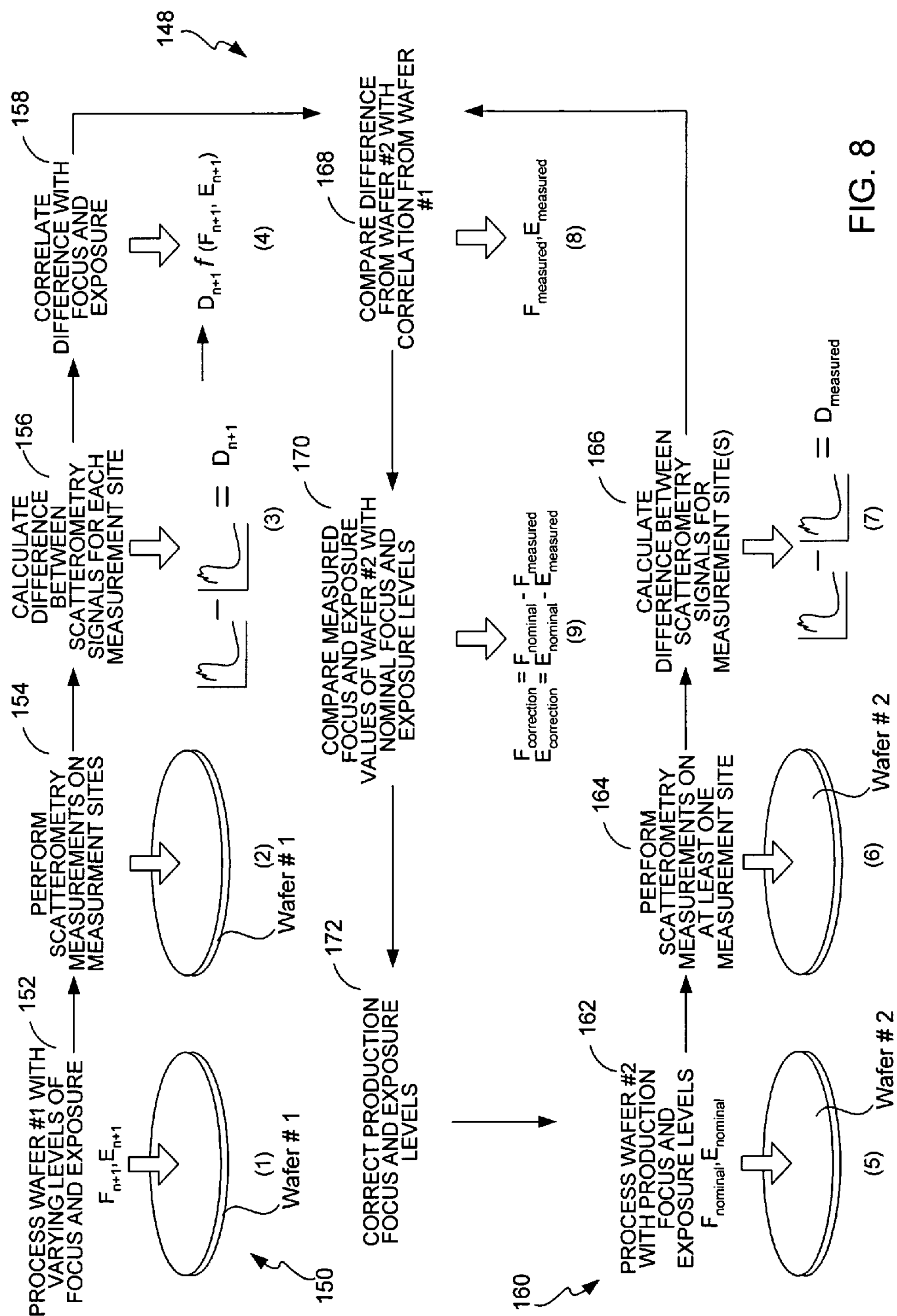
FIG. 8 is a schematic presentation of a method of monitoring focus and exposure, in accordance with one embodiment of the present invention.

FIG. 8 is a schematic presentation of a method of monitoring focus and exposure 148, in accordance with one embodiment of the present invention. The method 150 generally begins at step 152 where a first wafer is processed with varying levels of focus and exposure. The processing generally includes printing a plurality of scatterometry measurement sites in a layer of photo resist with a lithography system (e.g., on a focus exposure test matrix wafer). The scatterometry measurement target groups include at least two grating structures having different process responses (e.g., periodic structures such as line space or grid space gratings). Following step 152, the process flow proceeds to step 154 where scatterometry measurements are performed on the scatterometry measurement target groups and more particularly each of the grating structures located in the measurement target groups. This is generally accomplished with a scatterometry measurement tool such as those based on spectroscopic ellipsometry or spectroscopic reflectometer (see for example FIG. 11), or angle resolved ellipsometer, or angle resolved reflectometer. The scatterometry measurements are generally in the form of measured spectra.

Following step 154, the process flow proceeds to step 156 where a difference between the measured spectra is calculated for each measurement target group. For example, the difference between a first spectra formed from a first grating structure and second spectra formed from a second grating structure may be found for each measurement target group. Following step 156, the process flow proceeds to step 158 where the differences are correlated with focus and exposure. For example, a first difference may be correlated with a first focus and exposure setting and a second difference may be correlated with a second focus and exposure setting (and so on). The difference is a function of focus and exposure.

The method continues in a separate process flow 160 that generally occurs after steps 152-158. The separate process flow may occur during a production run. The separate process flow 160 generally begins with step 162 where a second wafer is processed with production focus and exposure settings. The production focus and exposure values generally correspond to what's believed to be the best focus and exposure for the product device on the photolithography system being used. The processing generally includes printing a plurality of scatterometry measurement groups in a layer of photo resist with a lithography system (e.g., on a production wafer). The lithography system may for example be the same system used in step 152.

Following step 162, the process flow proceeds to step 164 where scatterometry measurements are performed on the scatterometry measurement target groups. The scatterometry measurement target groups include at least two grating structures with different process responses. The grating structures may for example correspond to periodic structures such as line space or grid space gratings. The measurement is generally accomplished with a scatterometry measurement tool. The scatterometry tool may be the same scatterometry tool used in step 154. The scatterometry measurements are generally in the form of measured spectra.

Following step 164, the process flow proceeds to step 166 where a difference between the measured spectra is calculated for the grating structures located within the measurement target group.

Following step 166, the process flow proceeds to step 168 where the difference found in step 166 is compared with the correlation found in step 158. This generally results in a measured value for focus and exposure. The measured values generally correspond to the "effective" values for focus and exposure of the lithography system although production focus and exposure values were set. As should be appreciated, focus and exposure settings may fluctuate or change over the course of a production run, from run to run, or the life of the lithography tool. The best production settings for focus and exposure may be different for different lithography systems, due in part to different calibrations of focus and exposure between lithography tools. It should be noted that multiple differences may need to be found in order to solve for two unknowns such as focus and exposure. In order to obtain multiple differences, step 166 may be repeated for multiple measurement target groups. In cases such as this, the multiple differences found in step 166 are compared with the correlation found in step 158.

Following step 168, the process flow proceeds to step 170 where the measured focus and exposure values found in step 168 are compared with the nominal focus and exposure values. This typically results in a correction factor for both focus and exposure. Following step 170, the process flow proceeds to step 172 where the production focus and exposure values are corrected using the correction factor determined in step 170. The second process flow 160 may be performed continuously or incrementally over a production run to ensure that the integrated circuits printed thereon meet specified requirements. The first process flow, steps 152-158, may be performed incrementally as needed to ensure that the correlations are accurate.

FIG. 9 is a method of determining optimal or best focus 172, in accordance with one embodiment of the present invention. The method 172 generally begins at block 174 where a target group is produced over a wide range of focus settings. The target group includes two or more different targets produced with the same pitch but different linewidths thereby producing targets with different sensitivities to focus. By way of example, a first target may be produced with a nominal linewidth and a second target may be produced with a thinner line width.

Figure 10A:
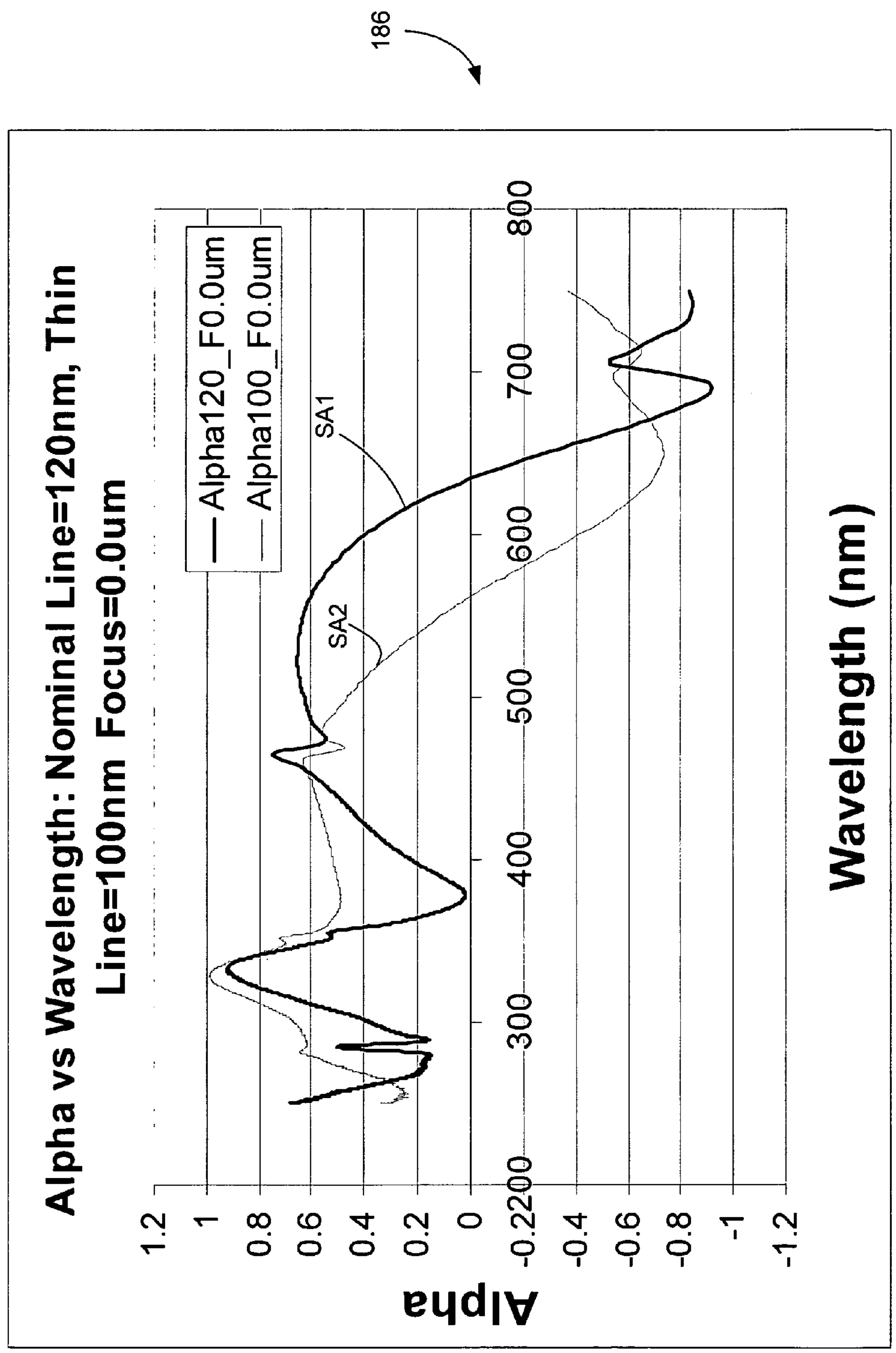
FIG. 10A is a graphical plot illustrating a pair of scatterometry signals produced with a target group having targets with the same pitch but different linewidths, in accordance with one embodiment of the present invention.
Figure 10B:
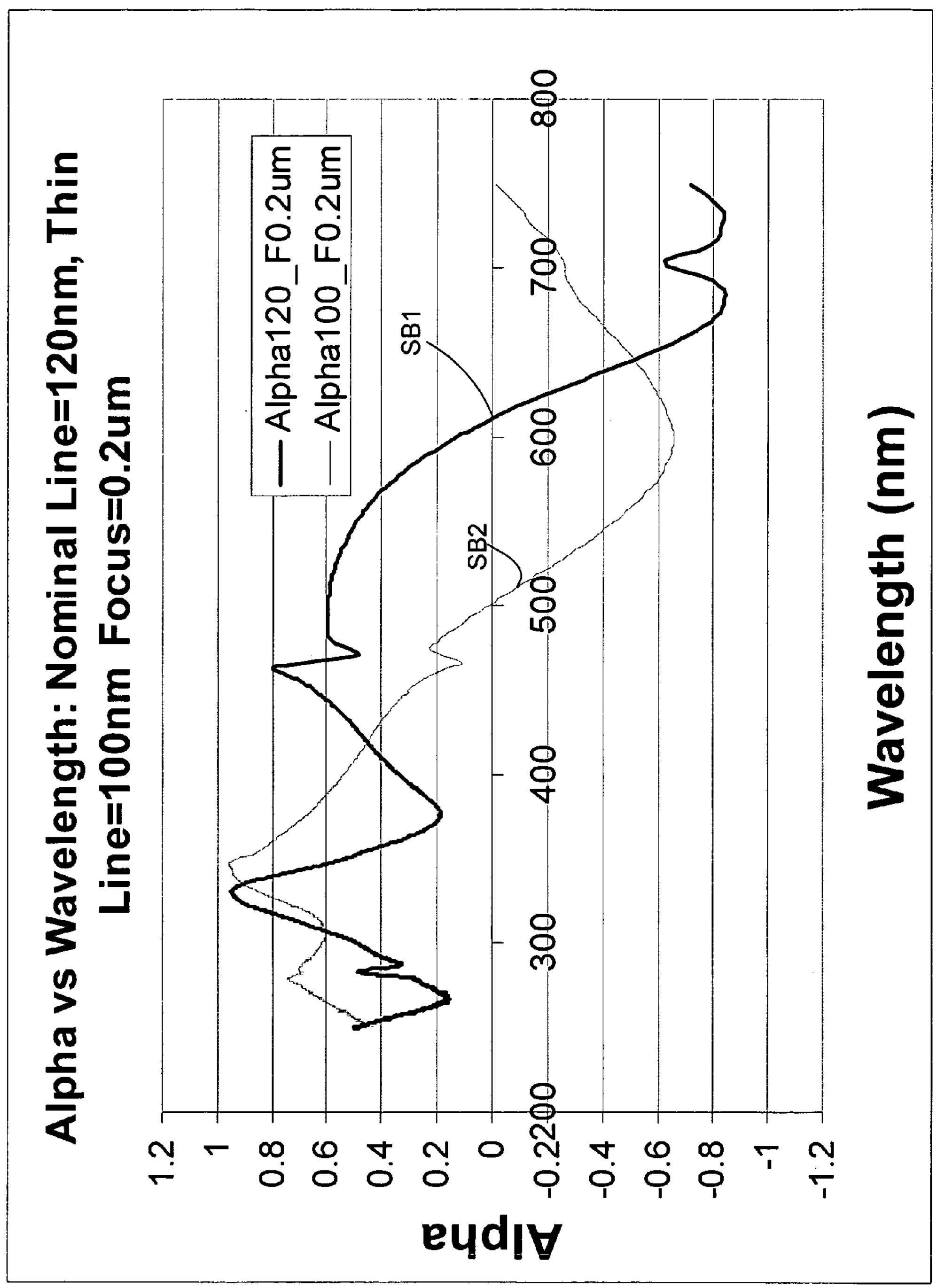
FIG. 10B is graphical plot illustrating a pair of scatterometry signals produced from targets with the same pitch but different linewidths, in accordance with one embodiment of the present invention.

Following block 174, the process flow proceeds to block 176 where scatterometry signals are obtained for each of the targets in the target groups (see FIGS. 10A and 10B).

Following block 176, the process flow proceeds to block 178 where difference signals are calculated for each target group. For example, the scatterometry signal produced from the first target can be subtracted from the scatterometry signal from the second target to produce a difference signal for each target group and therefore a difference signal for each focus setting. The difference signal can be formed from the scatterometry signals in their entirety or it can be formed from a portion of the scatterometry signals (see FIG. 10C).

Following block 178, the process flow proceeds to block 180 where the root mean squared difference (RMSD) for each difference signal is calculated. RMSD is generally well known in the art and will not be described in greater detail.

Following block 180, the process flow proceeds to block 182 where a relationship is formed between the RMSDs and the focus settings. The relationship may be in the form of an equation or a graphical plot (see FIG. 10D or 10E).

Following block 182, the process flow proceeds to block 184 where the relationship is used to determine best focus. Best focus generally occurs where the RMSD at its minimum (see FIG. 10D or 10E).

FIG. 10A is a graphical plot 186 illustrating a pair of scatterometry signals SA1 and SA2 produced with a target group having targets with the same pitch but different linewidths. The first scatterometry signal SA1 was produced by measuring a grating target that was produced by using a masking structure designed to produce 120 nm linewidths. The second scatterometry signal SA2 was produced by measuring a second grating target that was produced by using a second masking structure designed to produce 100 nm linewidths with the same pitch as the first grating target. The first and second target were produced in the same field and thus they were formed with the same focus setting of 0.00 μm (micron).

FIG. 10B is graphical plot 188 illustrating a pair of scatterometry signals SB1 and SB2 produced from targets with the same pitch but different linewidths. The scatterometry signals SB1 and SB2 were produced using the same grating structure set as in FIG. 10A, but with a different focus setting of 0.2 μm.

Figure 10C:
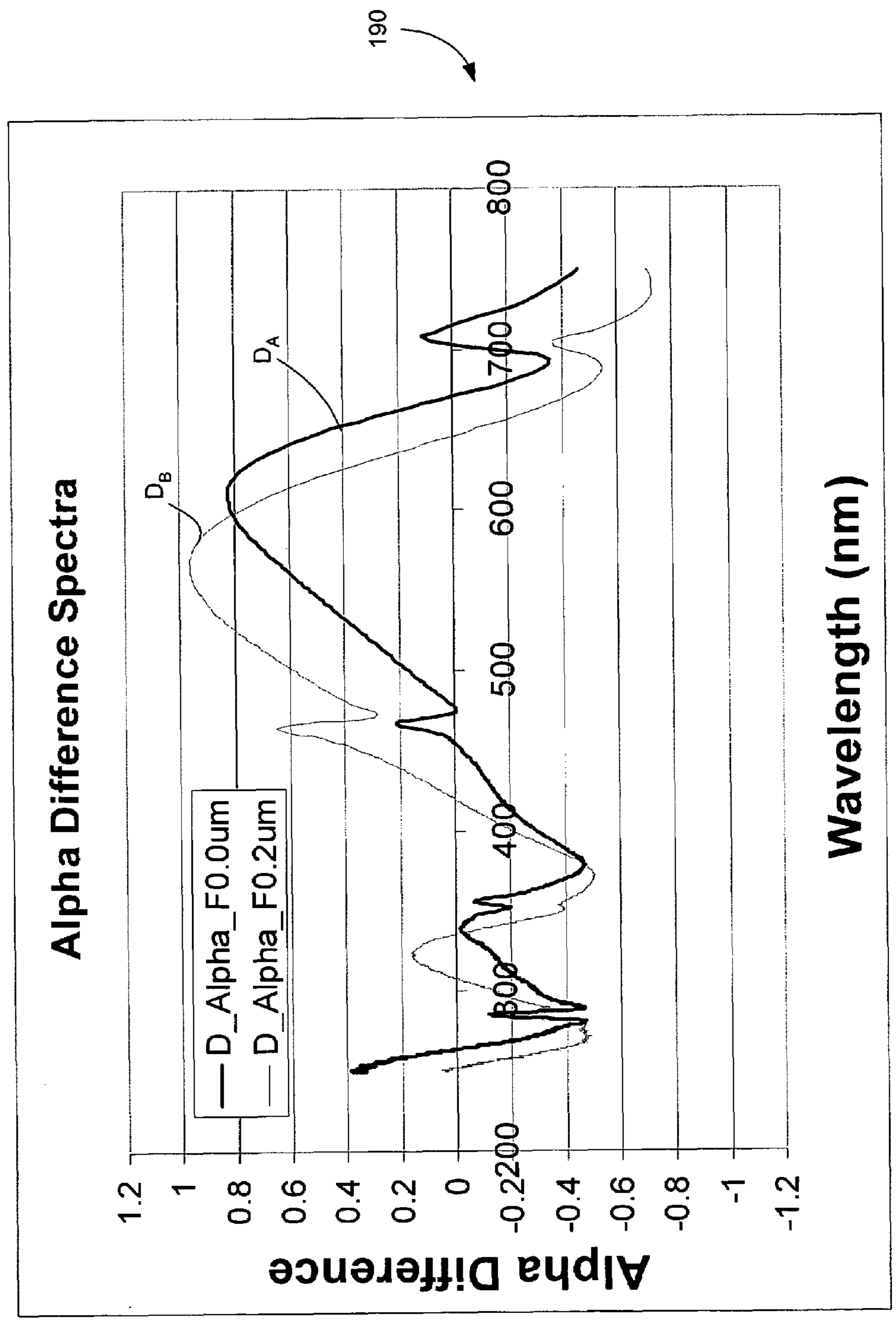
FIG. 10C is a graphical plot illustrating difference signal formed from the pair of scatterometry signals of FIG. 10A as well as difference signal formed from the pair of scatterometry signals of FIG. 10B, in accordance with one embodiment of the present invention.

FIG. 10C is a graphical plot 190 illustrating difference signal $D_A$ formed from SA1 and SA2 of FIG. 10A as well as difference signal $D_B$ formed from SB1 and SB2 of FIG. 10B. As shown, the difference signal is formed by subtracting alpha at various wavelengths between 250 and 750 nm.

Figure 10D:
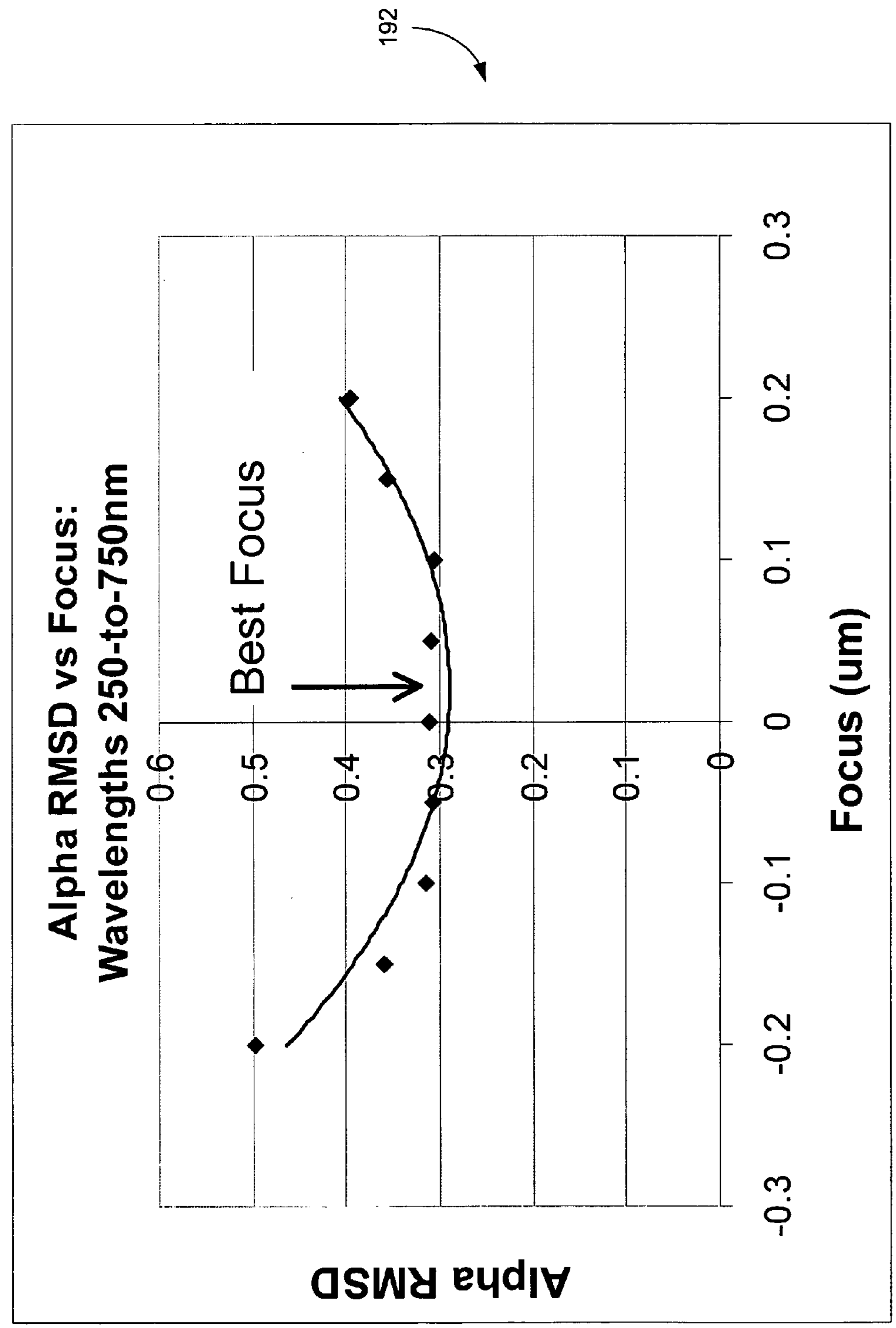
FIG. 10D is a graphical plot illustrating alpha RMSD versus focus, in accordance with one embodiment of the present invention.

FIG. 10D is a graphical plot 192 illustrating alpha RMSD versus focus. In the illustrated example, the alpha RMSD was calculated for difference signals formed at focus settings between 0.2 μm and −0.2 μm at increments of 0.05 μm. By way of example, alpha RMSD at 0.0 um was produced using the difference signal $D_A$ and the alpha RMSD at 2.0 μm was produced using the difference signal $D_B$ of FIG. 10C.

Figure 10E:
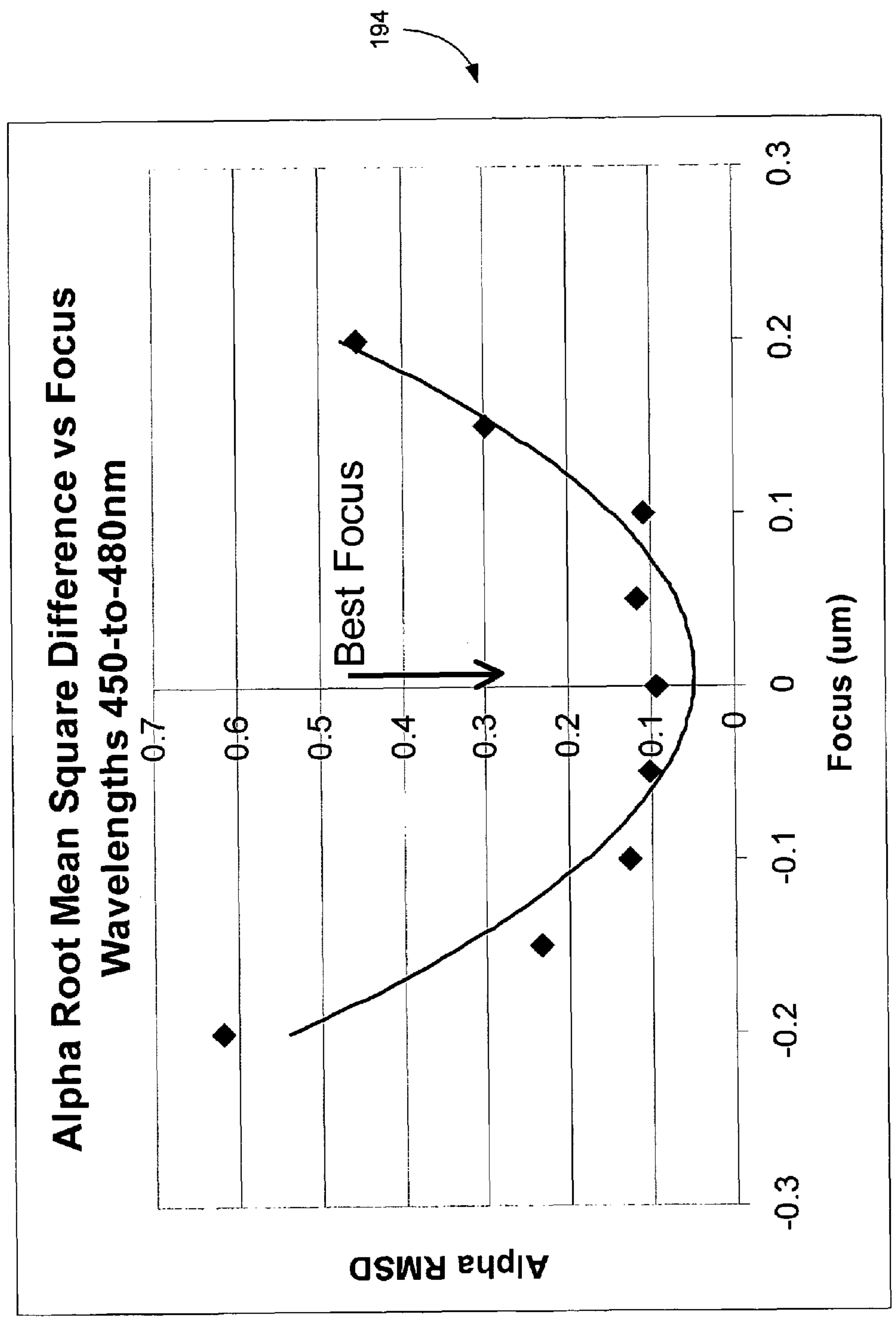
FIG. 10E is a graphical plot illustrating alpha RMSD versus focus, in accordance with one embodiment of the present invention.

FIG. 10E is a graphical plot 194 illustrating alpha RMSD versus focus. In the illustrated example, the alpha RMSD was calculated for difference signals formed at focus settings between 0.2 um and −0.2 um at increments of 0.05 um. Unlike FIG. 10D, however, the plot shown in FIG. 10E was produced using difference signals taken between wavelengths 450 and 480 nm rather than 250 and 750 nm as in FIG. 10D.

Figure 11:
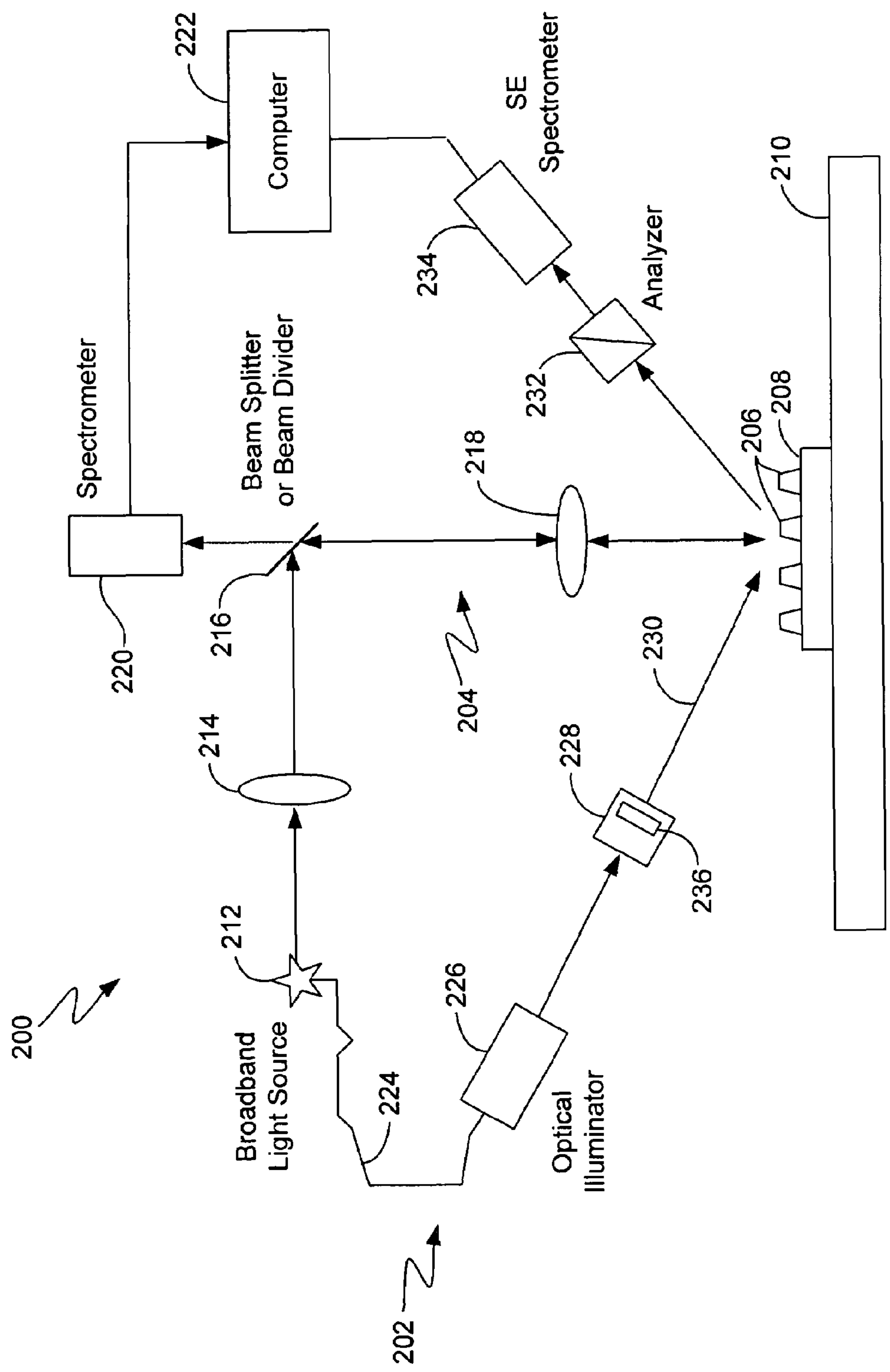
FIG. 11 is a schematic view of a spectroscopic scatterometer system, in accordance with one embodiment of the present invention.

FIG. 11 is a schematic view of a spectroscopic scatterometer system 200, in accordance with one embodiment of the present invention. The system 200 combines the features of a spectroscopic ellipsometer 202 and spectroscopic reflectometer 204, each of which may be used for measuring grating structures 206 disposed on a substrate or wafer 208. The grating structures 206, which are shown in a somewhat simplified format in the Figure, may be widely varied. The grating structure 206 may, for example, correspond to any of those grating structures described herein.

Both the spectroscopic ellipsometer 202 and spectroscopic reflectometer 204 may utilize a stage 210, which is used for moving the substrate 208 in the horizontal xy directions as well as the vertical z direction. The stage 210 may also rotate or tilt the substrate 208. In operation, the stage 210 moves the substrate 208 so that the grating structures 206 can be measured by the spectroscopic ellipsometer 202 and/or the spectroscopic reflectometer 204.

The spectroscopic ellipsometer 202 and spectroscopic reflectometer 204 also utilize one or more broadband radiation sources 212. By way of example, the light source 212 may supply electromagnetic radiation having wavelengths in the range of at least 230 to 800 nm. Examples of broadband light sources include deuterium discharge lamps, xenon arc lamps, tungsten filament lamps, quartz halogen lamps. Alternatively, one or more laser radiation sources may be used instead of or in combination with the broadband light source.

In the spectroscopic reflectometer 204, a lens 214 collects and directs radiation from source 212 to a beam splitter 216, which reflects part of the incoming beam towards the focus lens 218, which focuses the radiation onto the substrate 208 in the vicinity of a grating structure 206. The light reflected by the substrate 208 is collected by the lens 218, passes through the beam splitter 216 to a spectrometer 220. The spectral components are detected and signals representing such components are supplied to the computer 222, which computes the difference signals in a manner described above. The process parameters and process corrections may also be calculated by the same computer or by a different computer.

In the spectroscopic ellipsometer 202, the light source 212 supplies light through a fiber optic cable 224, which randomizes the polarization and creates a uniform light source for illuminating the substrate 208. Upon emerging from the fiber 224, the radiation passes through an optical illuminator 226 that may include a slit aperture and a focus lens (not shown). The light emerging from the illuminator 226 is polarized by a polarizer 228 to produce a polarized sampling beam 230 illuminating the substrate 208. The radiation emerging from the sampling beam 230 reflects off of the substrate 208 and passes through an analyzer 232 to a spectrometer 234. The spectral components of the reflected radiation are detected and signals representing such components are supplied to the computer 222, which computes the process parameters in a manner described above.

In the spectroscopic ellipsometer 202, either the polarizer 228 or the analyzer 232 or both may include a waveplate, also known as compensator or retarder (not shown). The waveplate changes the relative phase between two polarizations so as to change linearly polarized light to elliptically polarized light or vice versa.

In order to collect more information about the interaction of the incident polarized light 230 with the sample, it is desirable to modulate the polarization state of the light or modulate the polarization sensitivity of the analyzer or both. Typically this is done by rotating an optical element within the polarizer and/or analyzer. A polarizing element within the polarizer or analyzer may be rotated, or, if at least one of those assemblies contains a waveplate, the waveplate may be rotated. The rotation may be controlled by the computer 222 in a manner known to those skilled in the art. Although the use of a rotating element may work well, it may limit the system 202. As should be appreciated, the use of rotating elements may be slow, and because there are moving parts they tend to be less reliable.

In accordance with one embodiment, therefore, the polarizer 228 is configured to include a polarization modulator 236, such as photoelastic modulator (PEM), in order to produce a fast and reliable spectroscopic ellipsometer. The polarization modulator replaces the rotating waveplate. The polarization modulator 236 is an optical element that performs the same function as a rotating waveplate, but without the costly speed and reliability problems. The polarization modulator 236 allows electrical modulation of the phase of the light without mechanically rotating any optical components. Modulation frequencies as high as 100 kHz are readily attainable.

In an alternative embodiment, the analyzer 232 is configured to include a polarization modulator such as a PEM (Photoelastic Modulator) that can be modulated electrically. In yet another embodiment, both the polarizer and analyzer contain polarization modulators, such as PEMs, that are modulated at different frequencies.

Because the polarization modulator 236 can modulate at such a high frequency, the polarization modulator 236 may be used to perform various techniques, which would otherwise be too slow. For example, the difference between the polarized reflectivity of two structures may be obtained. To do this, a PEM may be combined with an acoustic optical modulator (AOM), where the AOM rapidly moves between the two structures while modulating the polarization state at a different (but related, such as multiple or submultiple) frequency. Signals at the sum and the difference of the PEM and AOM modulation frequencies contain useful information and can be detected with high signal-to-noise by synchronous detection. Alternatively the AOM on the incident beam could be used in combination with a PEM in the analyzer.

Although not shown, the rotating waveplate may also be replaced by a polarization modulator in other types of scatterometric systems as for example a polarization sensitive reflectometer.

Figure 12:
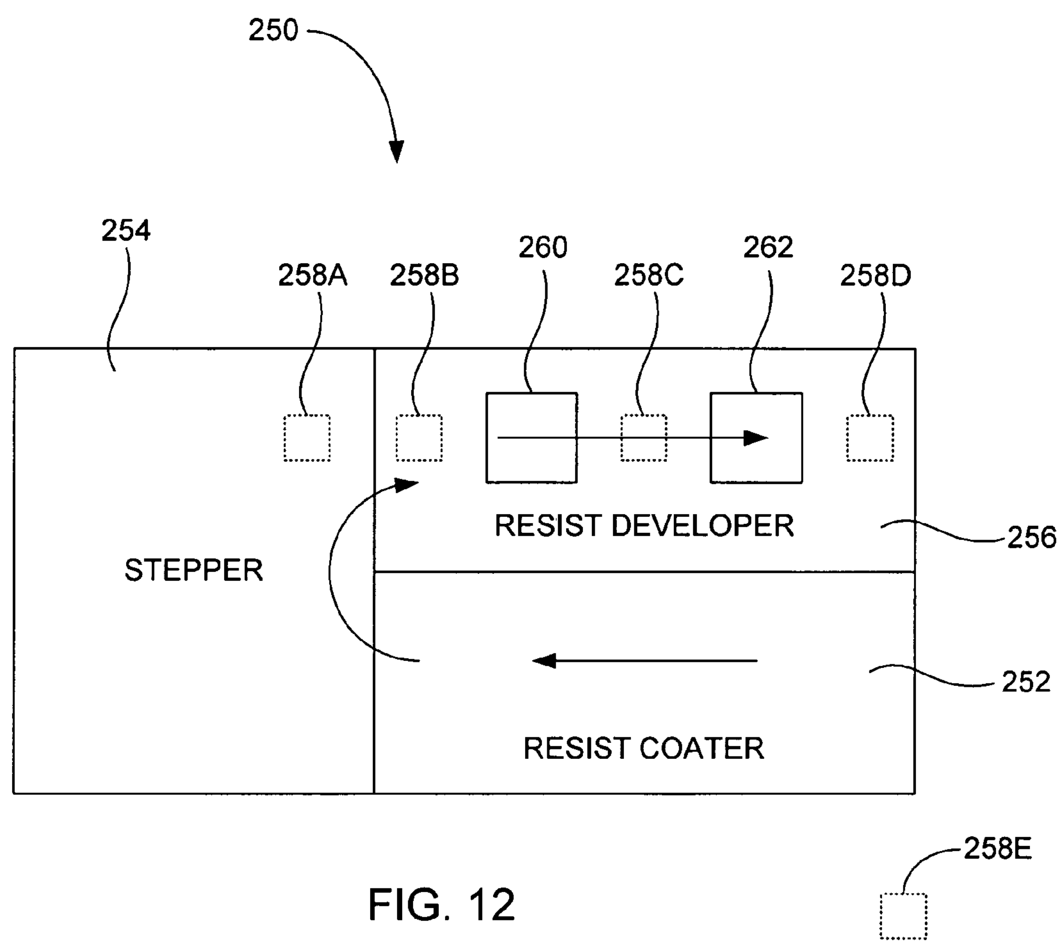
FIG. 12 is a diagram of a photolithographic processing system, in accordance with one embodiment of the present invention.

FIG. 12 is a diagram of a photolithographic processing system 250, in accordance with one embodiment of the present invention. The photolithographic system 250 generally includes a resist coater 252 that coats a film (photo resist) on wafer, a stepper 254 that exposes the film and a resist developer 256 that develops the film on wafer, thereby yielding a printed pattern. In operation, one or more wafers are sent through resist coater 252 where resist is applied thereto. Once resist has been placed on the wafer, the wafer is introduced into the stepper 254. While in the stepper, one or more fields are formed on the wafer. Each field includes patterns of the product being formed and at least one measurement target group including a pair of grating structures with different process responses. When producing product material, the fields are generally formed using nominal production values of focus and exposure. After the patterns have been formed on the wafer, the wafer is sent to the resist developer 256. While in the resist developer 256, the wafer passes through a post exposure bake 260 and a developer 262. Once developed, the wafer and its pattern can be further processed in another system. By way of example, the wafer may be etched or materials may be deposited thereon.

The photolithographic system 250 also includes a scatterometry tool 258 configured to provide useful information about process parameters used in the stepper 254 as for example focus and exposure. The scatterometry tool 258 may for example correspond to the system shown in FIG. 11. The scatterometry tool 258 may be configured to measure the latent image of the pattern, a partially developed pattern or a fully developed pattern. If latent image, then the scatterometry tool 258 may be placed at the end of the stepper 254 or at the beginning of the resist developer 256 (as indicated by reference numbers 258*a* and 258*b*, respectively). If a partially developed, then the scatterometry tool 258 may be placed after the post exposure bake 260 (as indicated by reference number 258*c*). If fully developed, then the scatterometry tool 258 may be placed after the developer 262 (as indicated by reference number 258*d*). Alternatively, the scatterometry tool 258 may be a stand alone tool or a tool that is integrated with a metrology cluster tool (as indicated by reference number 258*e*).

FIGS. 13A-13L are diagrams of masking systems capable of producing target groups. The masking systems include masking structures configured to produce targets with different process responses. Because they have different process responses, the differential targets and more particularly measurements taken therefrom may be compared to ascertain information about the process parameters associated with the process responses. For example, scatterometry measurements for each target may be taken and thereafter a difference signal may be formed based on the differences between the scatterometry measurements. As should be appreciated, the difference between scatterometry measurements is due at least in part to the different process responses and thus so is the difference signal. The number of targets and the magnitude and sense of their corresponding differences may be chosen in any suitable manner so that the techniques of the present invention may be practiced to determine one or more process parameters.

The different process responses may be created by utilizing similar but different masking structures. For example, one of the masking structures may contain different feature parameters or assist features when compared to the other masking structure thus making one of the targets more or less sensitive to a particular process parameter when compared to the other target. One or more of the masking structures may be designed with asymmetric optical proximity correction structures (or other wavefront engineering methods or features) to provide more sensitive information on the direction of focus errors.

The target groups may be printed on a focus exposure test matrix wafer, a test wafer or a production wafer. The focus exposure matrix wafer as well as the test wafer are generally used for testing the lithography equipment or producing calibration data rather than for generating a product. Any number of target groups may be positioned on the wafers. Generally speaking, about 1 to about 10 target groups per field may be used on production wafers while up to 1000's of target groups per field may be used on focus exposure matrix wafer and test wafers. The target groups may be patterned using suitable photolithographic techniques. In most cases, the target groups are printed in a layer of photo resist using a stepper or scanner lithography system. Line end shortening techniques may be used. Line end shortening can be used as part of a methodology for designing targets with different sensitivities to focus and exposure. Line end shortening is commonly used for focus exposure tracking using a CD-SEM or optical microscope. Line end shortening techniques with positive and reserve tone measurement structures allow the separation of exposure from focus.

Measurements of grating target sets including both normal positive tone grating structures and reverse tone grating structures provides more information that may be used to provide better separation of the effects of different process parameters, for example, photolithography focus and exposure. This concept of using positive and reverse tone targets to separate the effects of focus and exposure is well understood for line end shortening targets measured with optical or electron microscopes. The effects of line-end shortening for periodic scatterometry structures are similar, so analysis of properties of scatterometry spectra from positive and reverse tone targets can provide information on both focus and exposure process parameters.

Methods for adjusting the sensitivity of line-end shortening targets to lithographic process changes by using wavefront engineering features, which may include optical proximity correction structures, have been described previously, by Bendik et al in U.S. Pat. No. 6,673,638, which is herein incorporated by reference. These methods may be applied to design and produce mask structures that produce scatterometry grating structures on the wafer that have different lithographic process sensitivities. Bendik et al is hereby incorporated in its entirety.

Figure 13A:
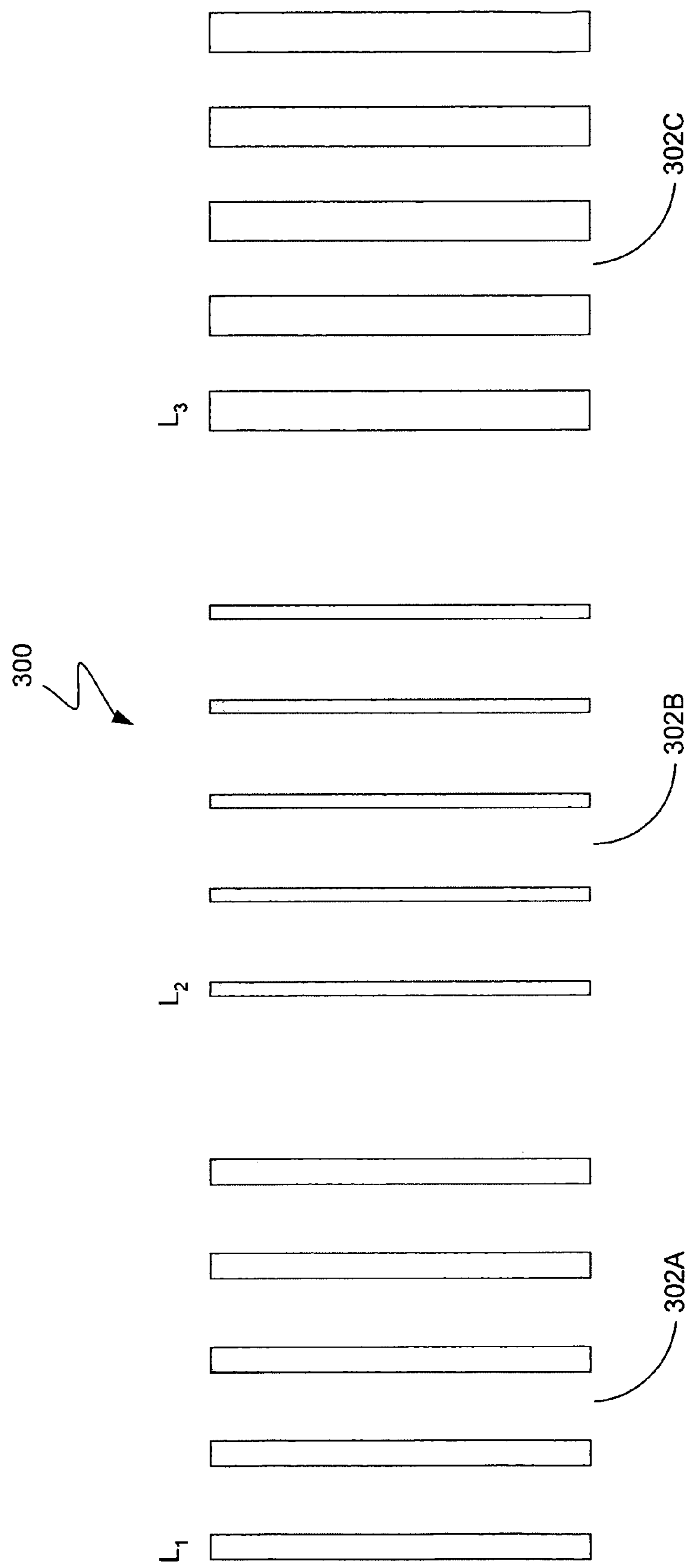
FIGS. 13A-13L are diagrams of a plurality of scatterometry measurement target groups or grating structure sets, in accordance with multiple embodiments of the invention.

FIG. 13A shows a masking system 300 for creating a target group. The masking system 300 contains a plurality of different masking structures 302, each of which produces a line grating with the same pitch PI, but different line widths CD1, CD2 and CD3. As shown, a first masking structure 302A has linewidth L1 capable of producing a nominal linewidth CD1, a second masking structure 302B has linewidth L2 capable of producing a thinner linewidth CD2 and a third masking structure 302C has linewidth L3 capable of producing a thicker linewidth CD3. The nominal linewidth CD1 is typically chosen to produce lines close to the design features, and may even be a device feature. In general, nominal means that the feature is close to process capability, sensitive to focus, but able to be printed over reasonable process range. Because the masking structures 302 produce different line widths CD, each of the line gratings will have different process responses. As should be appreciated, thinner line widths CD2 are more sensitive to focus and thicker line widths CD3 are less sensitive to focus. Because the targets have the different line widths and thus different process responses, the scatterometry signal produced thereform will be different. Difference signals can be generated between each of the scatterometry signals in order to obtain information about focus. This is represented by the following equations:

$$S1(P1,\ CD1)-S2(P1,CD2)=D1$$

$$S1(P1,\ CD1)-S3(P1,CD3)=D2$$

$$S2(P1,\ CD2)-S3(P1,CD3)=D3,\text{ where}$$

S1 is the scatterometry signal produced by the first grating

S2 is the scatterometry signal produced by the second grating

S3 is the scatterometry signal produced by the third grating.

In order to ascertain even more information about focus, different masking systems may be used to produce different target groups having different pitches. For example, a first target group T1 may contain three targets with the same pitch P1, but differing linewidths CD1, CD2 and CD3, a second target group T2 may contain three targets with the same pitch P2, but differing linewidths CD4, CD5 and CD6, and a third target group T3 may contain three targets with the same pitch P3, but differing linewidths CD7, CD8 and CD9. This is represented by the following equations:

$$S1(P1,\ CD1)-S2(P1,CD2)=D1$$

$$S1(P1,\ CD1)-S3(P1,CD3)=D2$$

$$S2(P1,\ CD2)-S3(P1,CD3)=D3 \qquad T1$$

$$S4(P2,\ CD4)-S5(P2,CD5)=D4$$

$$S4(P2,\ CD4)-S6(P2,CD6)=D5$$

$$S5(P2,\ CD5)-S6(P2,CD6)=D6 \qquad T2$$

$$S7(P3,\ CD7)-S8(P3,CD8)=D7$$

$$S7(P3,\ CD7)-S9(P3,CD9)=D8$$

$$S8(P3,\ CD8)-S9(P3,CD9)=D9 \qquad T3$$

Figure 13B:
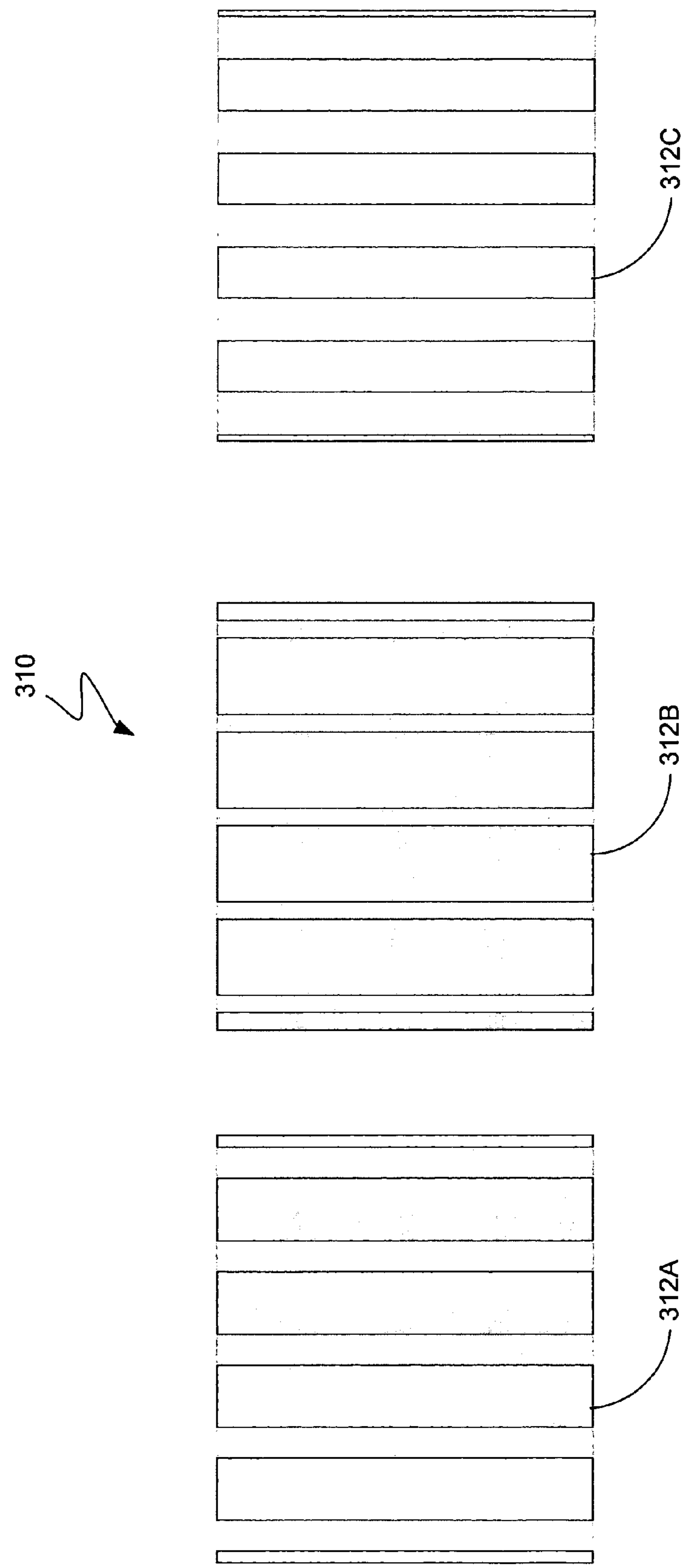

In some cases, the masking structures may create reverse tone targets rather than the positive tone targets. This may be done to help separate focus and exposure information. FIG. 13B shows a masking system 310 for creating a reverse tone target group. The masking system 310 contains a plurality of masking structures 312, each of which produces a reverse tone line target with the same pitch P1, but different linewidths CD1, CD2 and CD3 (resist width>space width). This type of target is sometimes referred to as a trench target.

Figure 13C:
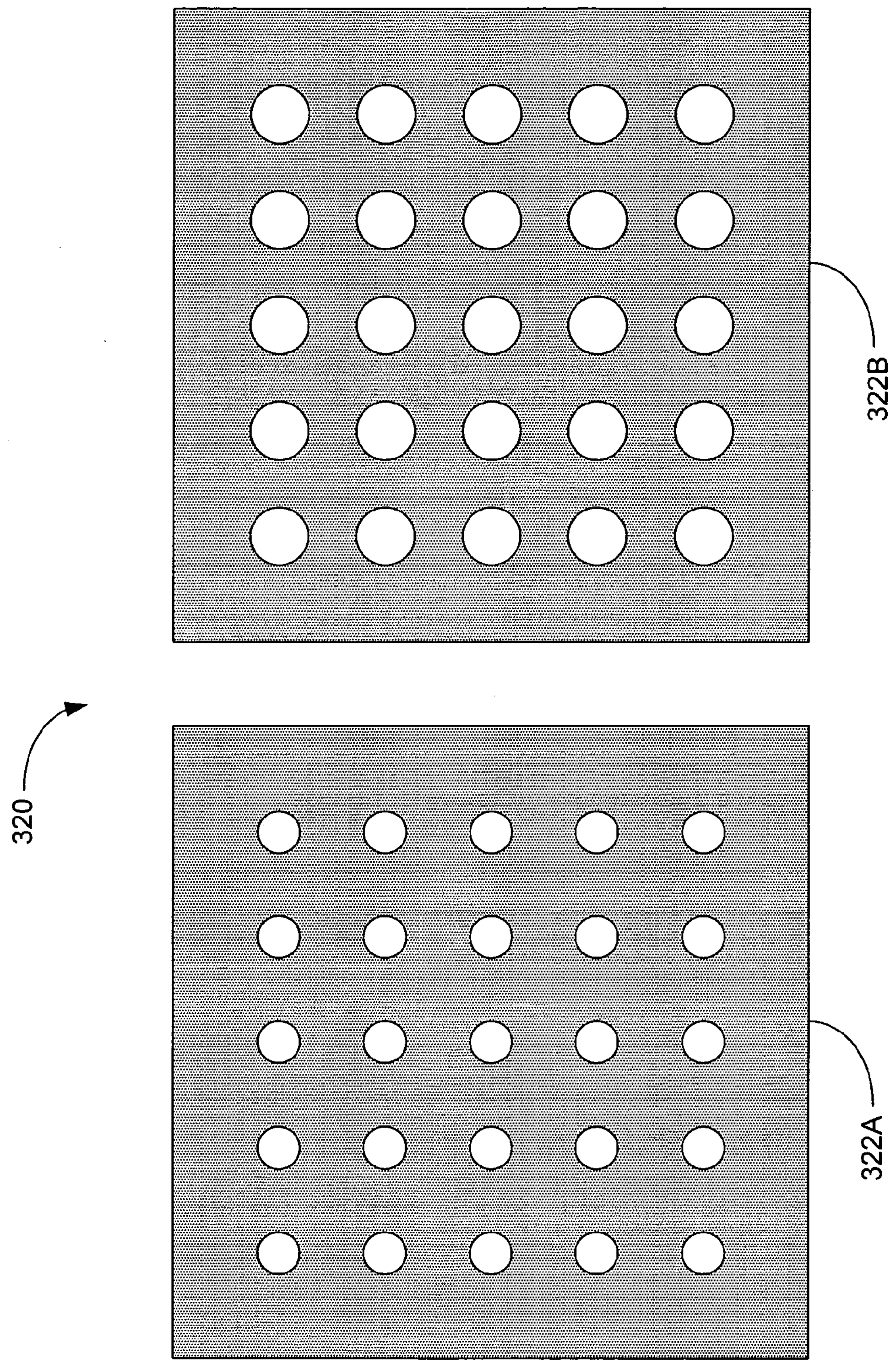

FIG. 13C shows a masking system 320 for creating a target group. The masking system 320 contains a plurality of different masking structures 322, each of which produces a contact or via target (cylindrical holes in resist) with the same pitch P1, but different diameters D1 and D2. A first masking structure 322A produces a contact target with contacts having nominal diameters D1 and a second masking structure 322B produces a contact target having a larger diameter D2. The nominal diameter D1 is typically chosen to produce contacts close to the design features, and may even be a device feature. Because the masking structures 322 produce different diameters D, each of the contact gratings will have different process responses. The larger diameter contacts are less sensitive to focus variation. At optimal focus (maximum device contact diameter at fixed exposure energy) the difference between the spectra measured for the targets should be minimum.

Figure 13D:
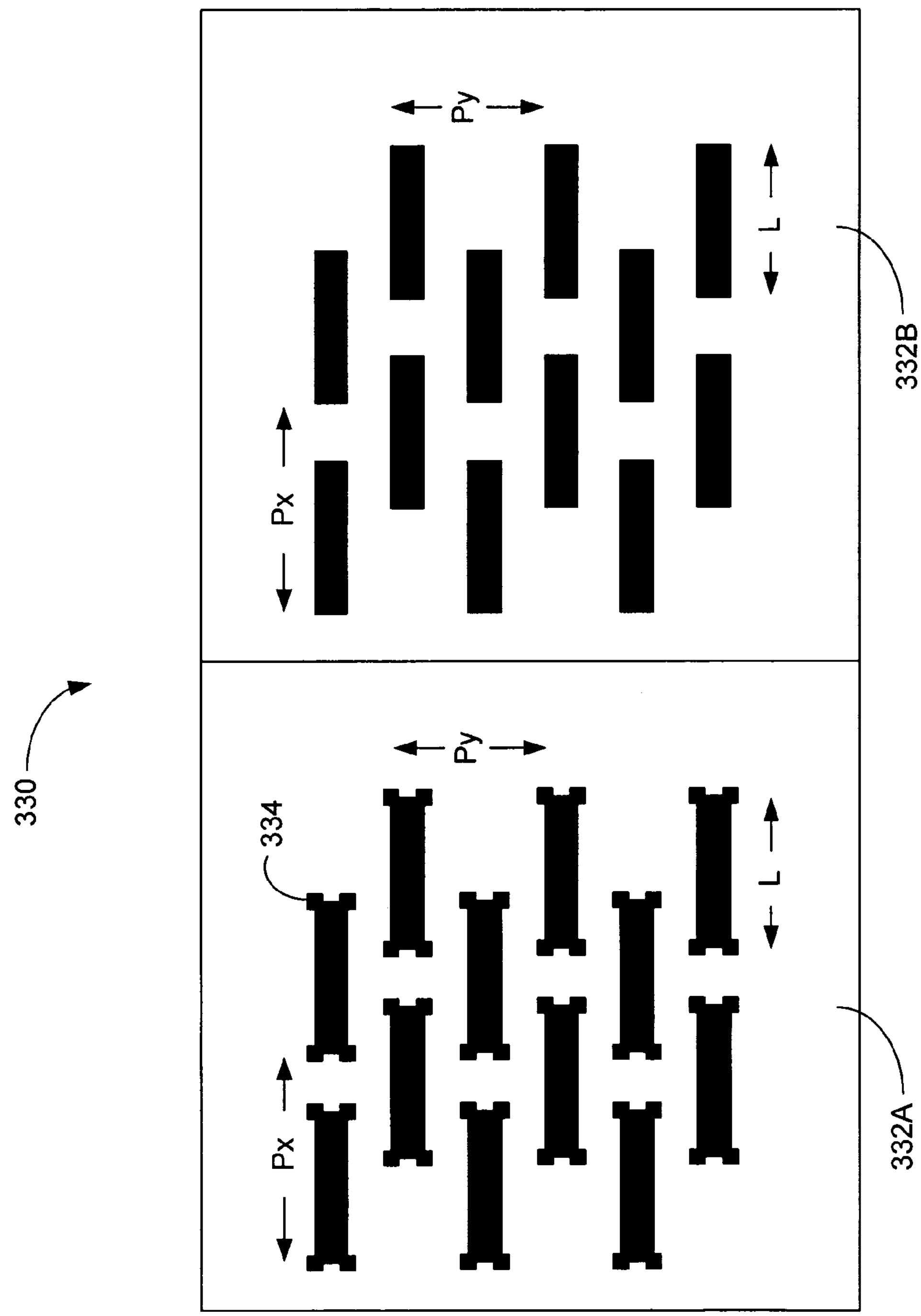

FIG. 13D shows a masking system 330 for creating a target group. The masking system 330 contains a plurality of masking structures 332, each of which produces a periodic target with the same two-dimensional periodicity Px and Py and layout, but different optical proximity corrections (OPC). As shown, the first masking structure includes serifs 334 while the second masking structure does not include serifs. The target without serifs should be more sensitive to focus variation. At optimal focus the difference between the spectra measured for the left and right measurement areas should be minimum.

Figure 13E:
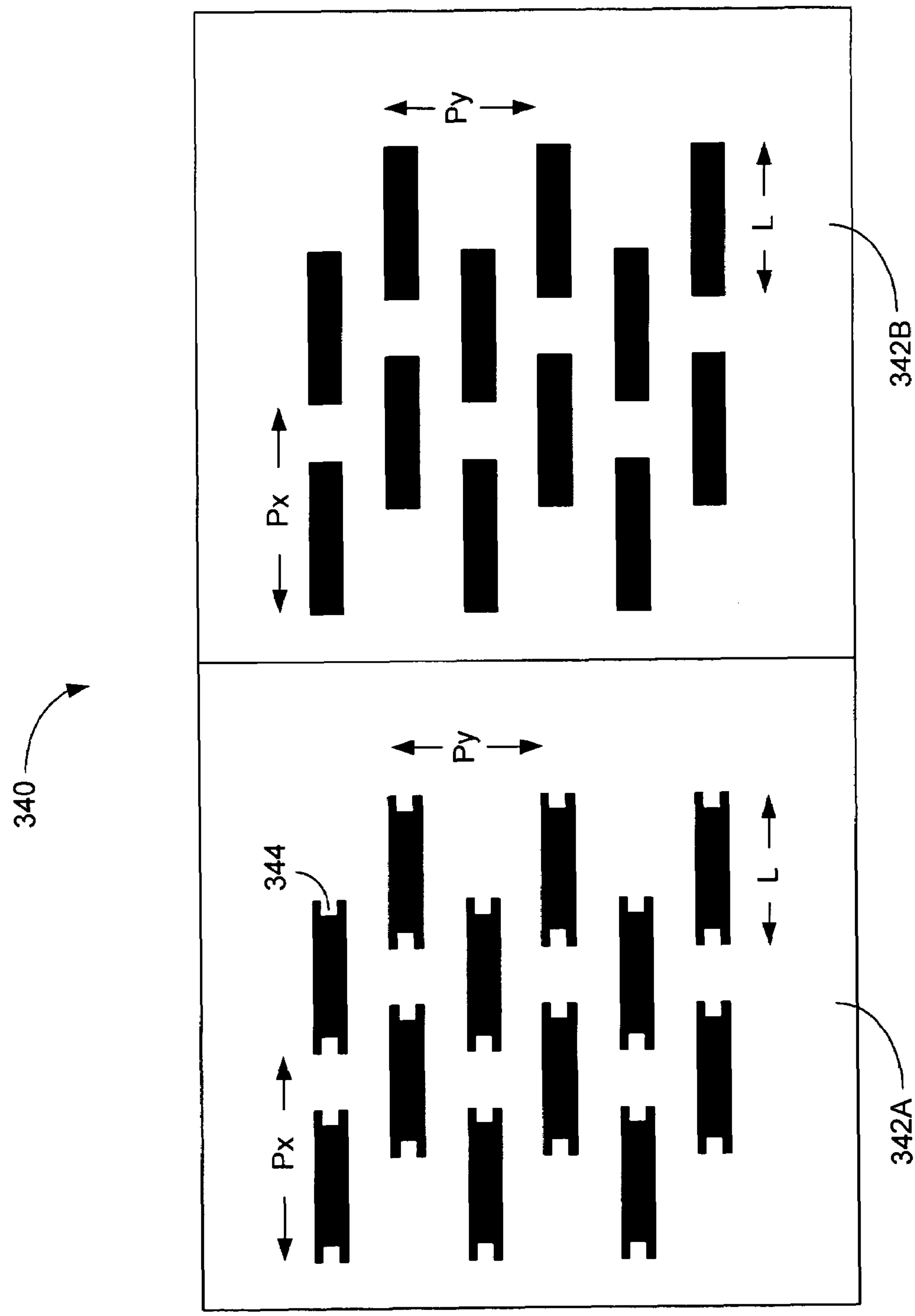

FIG. 13E shows a masking system 340 for creating a target group. The masking system 340 contains a plurality of masking structures 342, each of which produces a periodic target with the same two-dimensional periodicity Px and Py, and layout, but different optical proximity corrections (OPC). As shown, the first masking structure includes cut outs or anti-serifs 344 while the second masking structure does not include cut outs or anti-serifs. The target with cut outs should be more sensitive to focus variation. At optimal focus the difference between the spectra measured for the left and right measurement areas should be minimum.

Figure 13F:
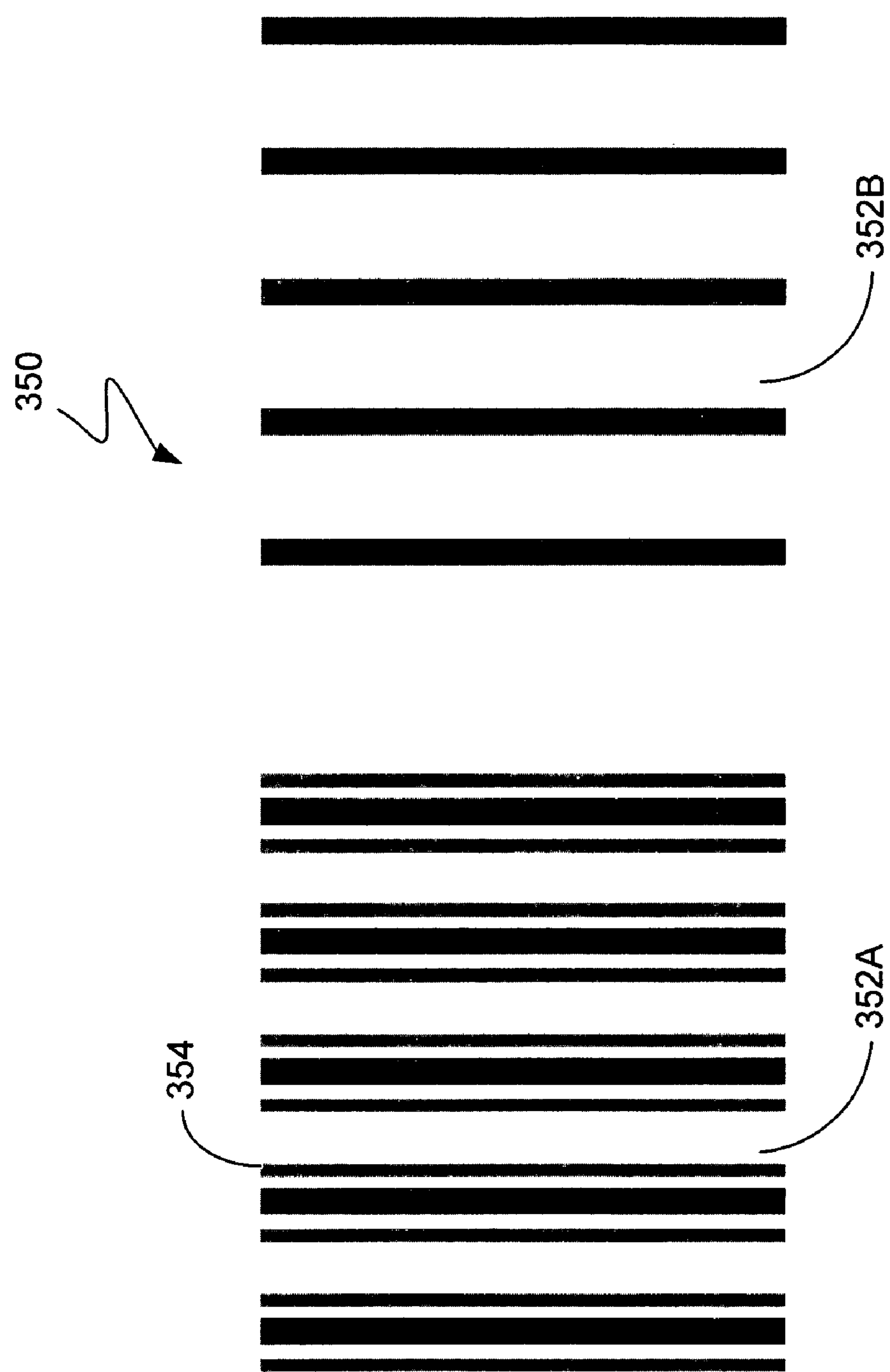

FIG. 13F shows a masking system 350 for creating a target group. The masking system 350 contains a plurality of masking structures 352, each of which produces a line target with the same pitch P1 and layout, but different optical proximity corrections (OPC). As shown, the first masking structure includes scattering bars 354 while the second masking structure does not include scattering bars. The target produced by the masking structure having scattering bars should be less sensitive to focus variation.

Figure 13G:
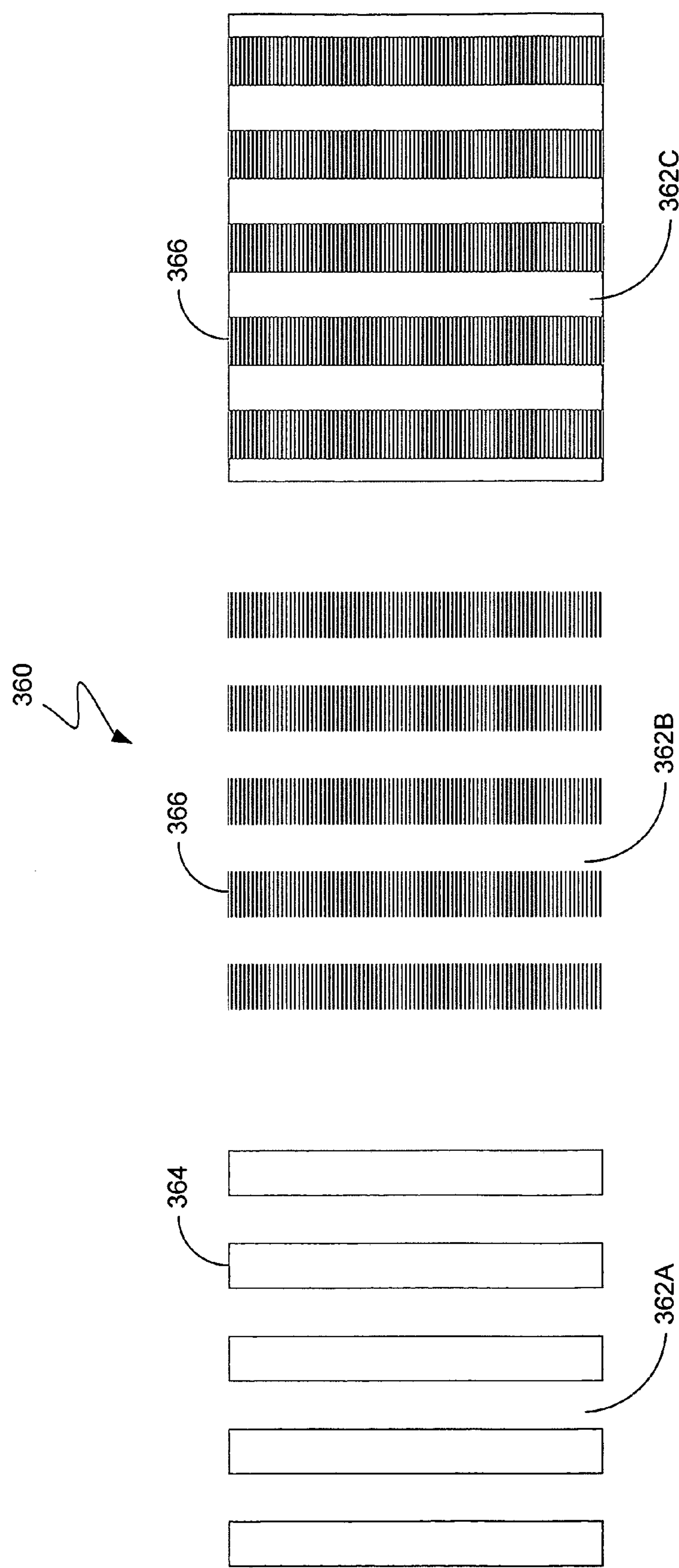

FIG. 13G shows a masking system 360 for creating a target group. The masking system 360 contains a plurality of masking structures 362, each of which produces a line target with the same pitch P1 and linewidth. The first masking structures is a grating formed by solid lines 364 while the second and third masking structures are gratings formed by segmented lines 366. The segmentation between the second and third masking structures are the same. The second masking structure differs from the third masking structure in that one of these structures produces a positive tone target and the other produces a negative tone target.

Figure 13H:
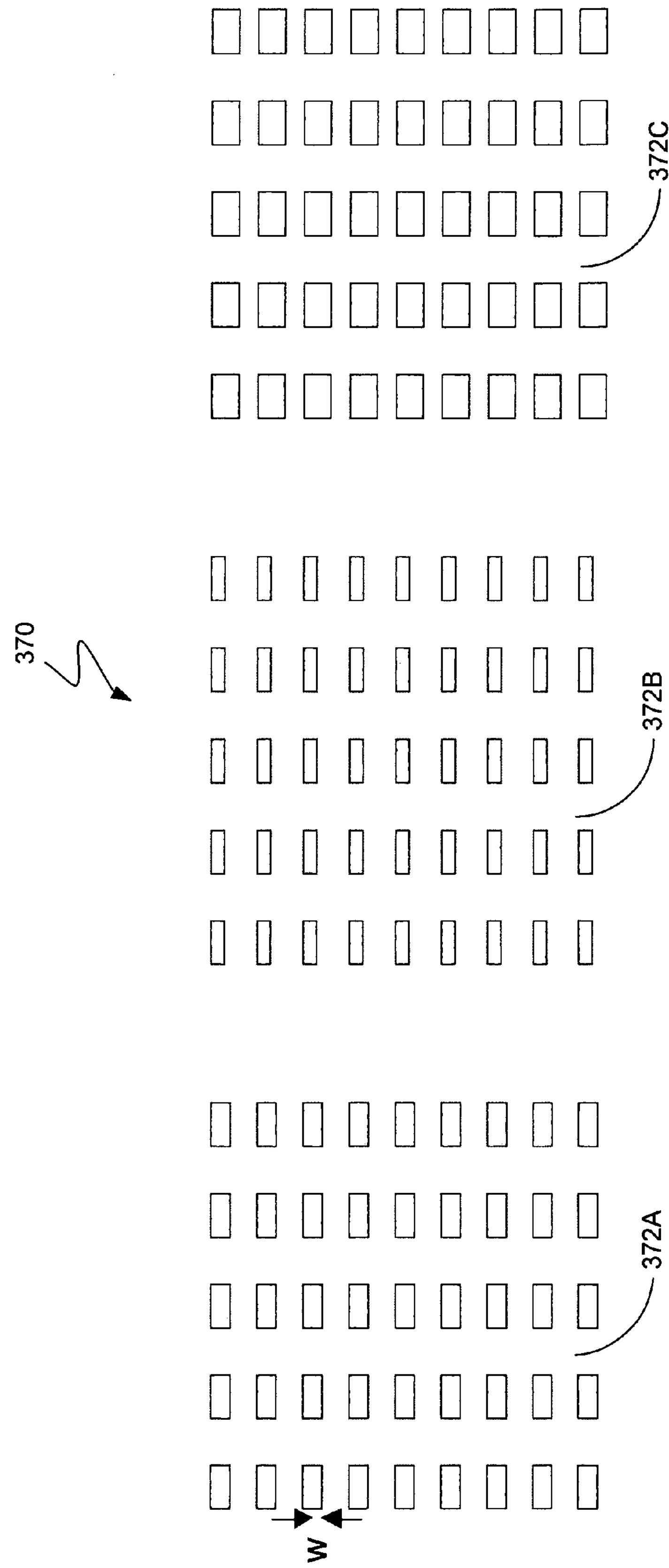

FIG. 13H shows a masking system 370 for creating a target group. The masking system 370 contains a plurality of masking structures 372, each of which produces a segmented line target with the same pitch P1 but different segment widths, w. The first masking structure includes nominal segmented lines, the second masking structure includes thinner segmented lines and the third masking structure includes wider segmented lines.

Figure 13I:
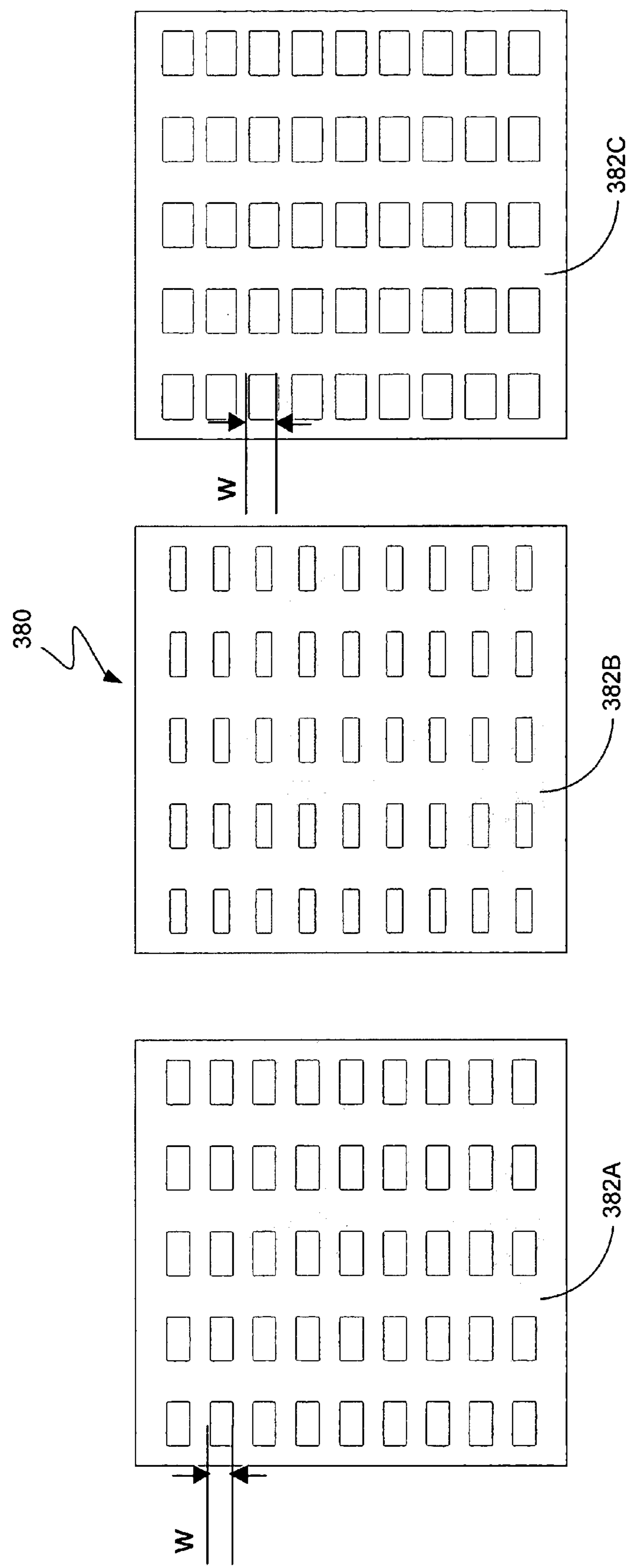

FIG. 13I shows a masking system 380 for creating a target group. The masking system 380 is similar to the masking system 370 shown in FIG. 13H except that it is configured to produce reverse tone targets.

Figure 13J:
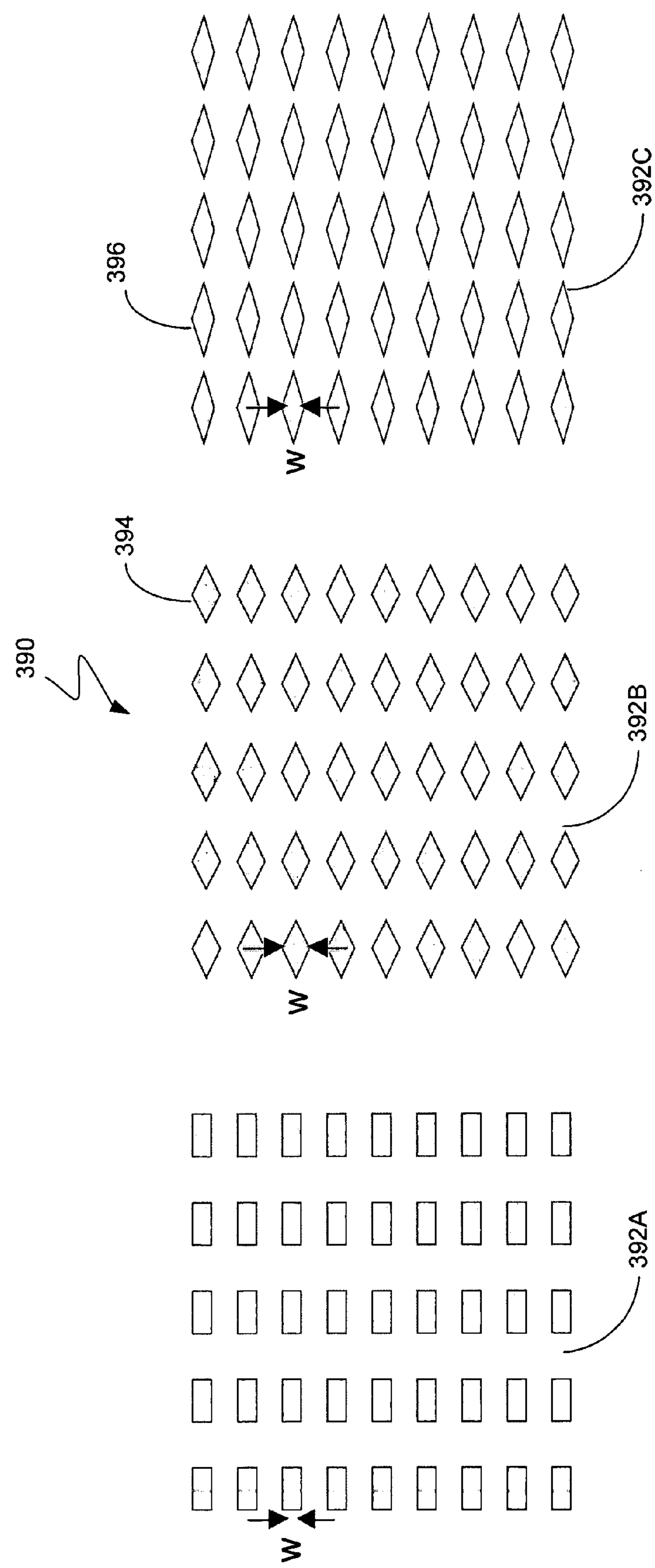

FIG. 13J shows a masking system 390 for creating a target group. The masking system 390 contains a plurality of masking structures 392, each of which produces a segmented line target with the same pitch P1 but different shape segments. The first masking structure includes nominal segmented lines, the second masking structure includes diamond shaped segments 394 and the third masking structure includes skinnier diamond shaped segments 396.

Figure 13K:
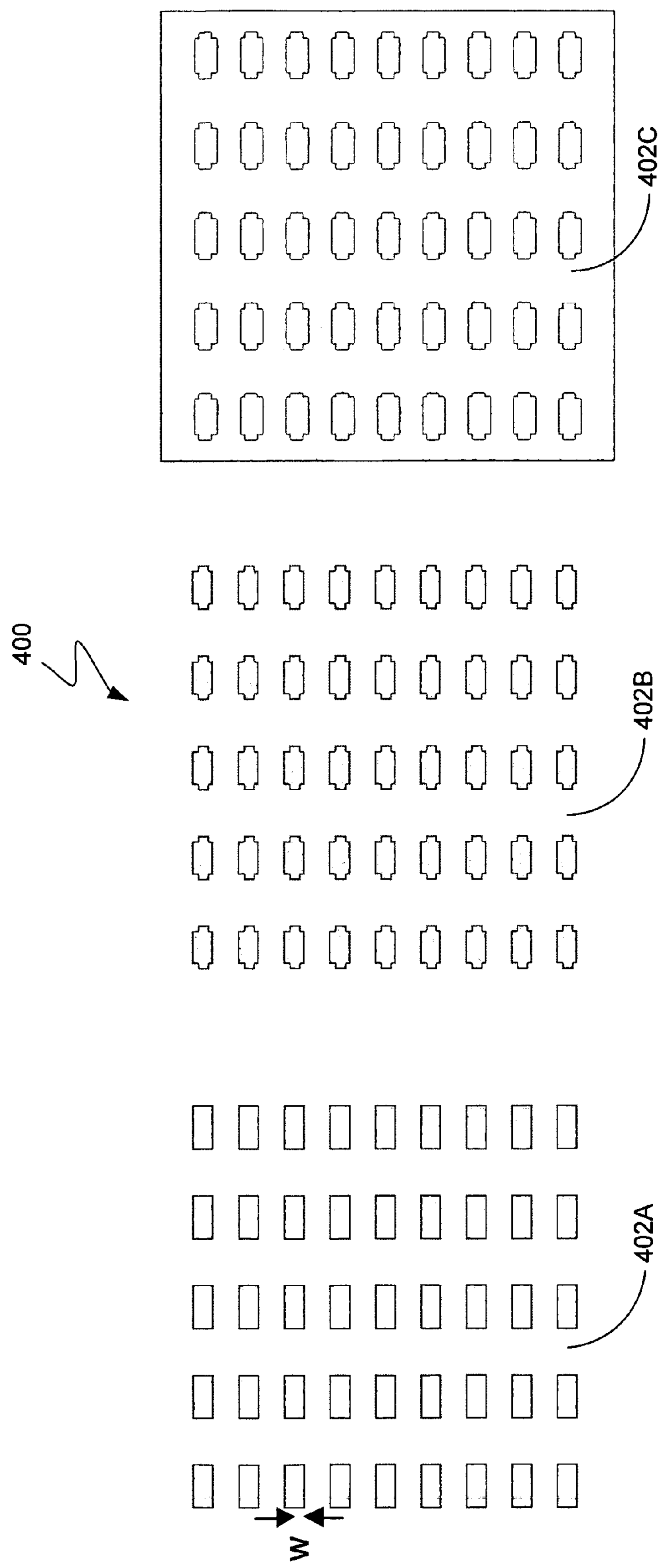

FIG. 13K shows a masking system 400 for creating a target group. The masking system 400 contains a plurality of masking structures 402, each of which produces a segmented line target with the same pitch P1 but different segment widths, w. The first masking structure includes nominal segmented lines, the second and third masking structure include nominal segmented lines with narrower line ends. The second and third masking structures differ in that one is configured to produce a positive tone target and the other is configured to produce a reverse tone target.

Figure 13L:
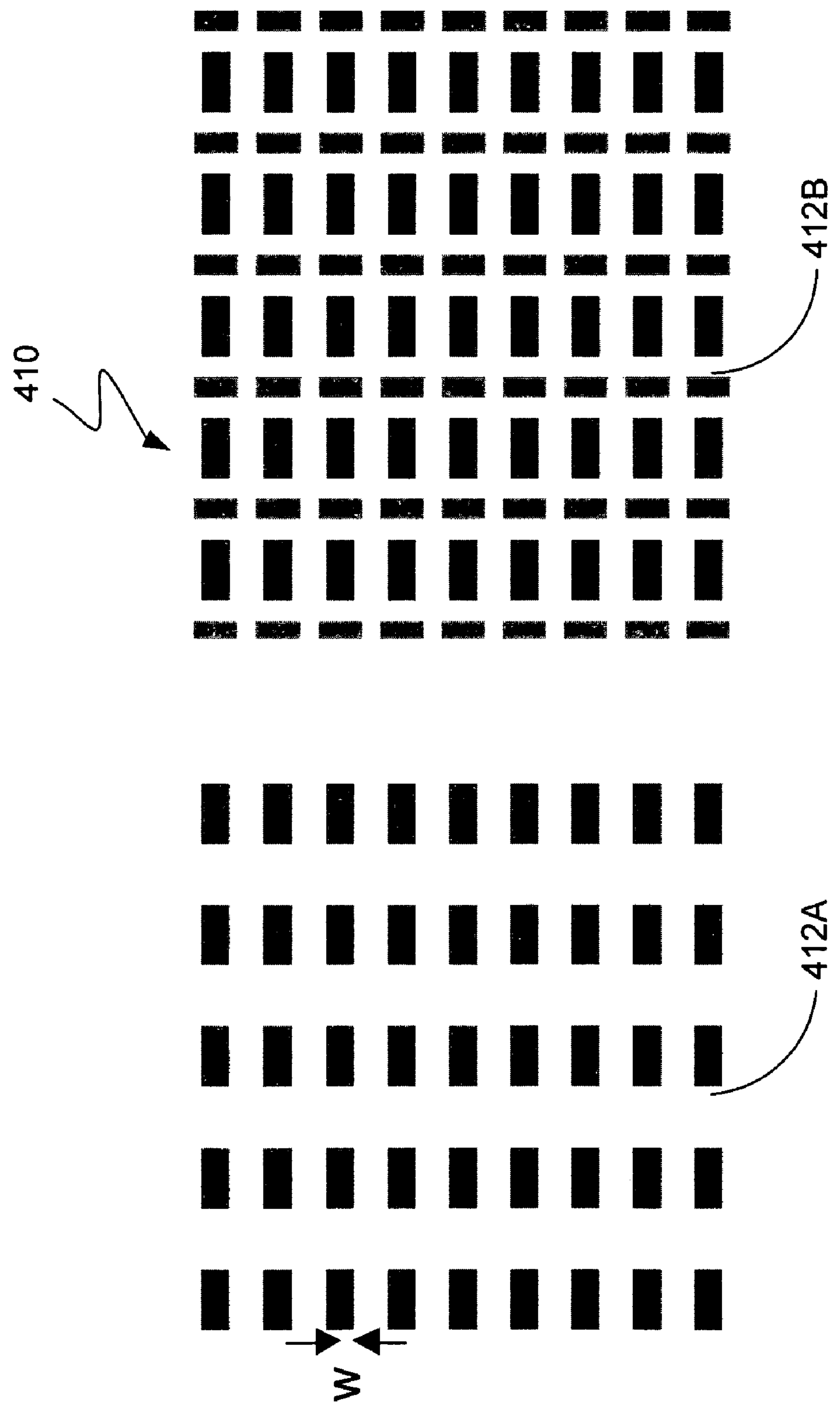

FIG. 13L shows a masking system 410 for creating a target group. The masking system 410 contains a plurality of masking structures 412, each of which produces a segmented line target with the same pitch P1 but different optical proximity correction (OPC). The first masking structure includes nominal segmented lines, and the second masking structure includes nominal segmented lines with sub resolution assist features (SRAFs). The second and third masking structures differ in that one is configured to produce a positive tone target and the other is configured to produce a reverse tone target.

Although not shown, the masking system may be constructed with different phase shifted masking structures. For example, a first phase shift masking structure may be configured to produce nominal minimal process sensitivity (as much like circuit feature process behavior as possible), a second phase shift masking structure may be configured to produce deliberate process sensitivity (unbalanced 0, 180 phase zone contributions), and a third phase shift masking structure may include binary features designed to have no dependence on feature position with focus (no pitch walk), same pitch as the first phase shift masking structure at best focus, and similar line widths as first phase shift masking structure at best focus.

Previously described methods of controlling processes using scatterometry measurements have concentrated on comparison of measured spectra to calculated theoretical spectra for model shape profiles, overlay and film stack. Alternatively, empirical scatterometry databases have been proposed where a collection of spectra are recorded from wafers that include process variation.

The disadvantage of the previous methods of process control using scatterometry measurements is the large number of parameters that must be included in the profile, and accurate film modeling to accurately determine the profile parameters that need to the controlled. For instance, using simple trapezoidal models for a 2-dimensional array of nominally rectangular line segments, the minimum number of target parameters that must be included is 5. If film thicknesses must be included as a model parameters, the number of parameters increases. Comparison of the measured spectra to the calculated spectra takes longer with more model parameters whether a library-based approach is used or a regression approach is used. A second disadvantages of the previous methods of scatterometry measurements based on comparing measured spectra to calculated spectra is the detailed knowledge of the film stack, film materials, and target element profiles required to calculated accurate theoretical spectra to compare to the measured spectra. A third disadvantage of empirical libraries is that they require creation of a set of reference wafers which will still be limited set that may not cover the range of process parameters that will be encountered in semiconductor manufacturing or process development.

One advantage of this invention is that is does not require calculation of theoretical spectra for model profile. Another advantage is enhanced sensitivity to certain profile parameters or process parameters compared to the spectral matching methods since there are no errors in the profile modeling to contribute to errors in the measurement. Another advantage is that errors in the modeling and calibration of scatterometry optical system contribute equally to measurements on all the scatterometry targets and are therefore cancelled out (to first order) when the difference signal is taken. Normal incidence measurements may also exhibit reduced sensitivity to film variation.

Another difference between this invention and the prior art is that this invention compares scatterometry spectra or signatures obtained from different scatterometry measurement or monitoring sites or areas within the same field to monitor the lithography process parameters. Properties of the comparison or difference signatures may be evaluated at a different focus setting and/or different exposure settings for the purposes of creating a calibration.

One advantage of the within-field, neighboring target differential scatterometry lithography monitoring method is that is may be used to monitor lithography process parameters (e.g. focus and/or exposure) on production wafers, enabling better process control than the prior art. Another advantage is that lithography process monitoring may be performed more frequently, several times per wafer, and several wafers per lot, every lot. More frequently process monitoring may enable better lithography process control. Lithography process monitoring with scatterometry method on production wafers may reduce the need for time-consuming, non-production tests such as focus-exposure matrix wafers and thereby increase the productivity of the lithography process system. The prior art also requests running a special test recipe on a wafer that cannot be sold as normal production material (may not be production material or it may require reworking the wafer and reprocessing the wafer as production material). Other prior art methods requires running a non-production wafer to determine the best focus on the wafer.

Another advantage over prior art methods that include modeling the scatterometry signatures is the elimination of the modeling which may be complex and time-consuming.

Another advantage over the prior art of comparing measured spectra to saved measured spectra (measured from one or more focus-exposure matrix wafers, for example) is that the difference signatures from 2 or more scatterometry structures constructed on the same wafer in close proximity have largely the same underlying structures. The film thickness and film compositions under neighboring scatterometry measurement areas are very similar and may be assumed to be the same if the scatterometry measurement are designed with nominally the same underlaying structures. Scatterometry signatures often sensitive to variations in the optical properties of underlying structures, including underlying film thicknesses, film compositions, structural features and the like. Comparison of measured scatterometry signatures with saved scatterometry signatures is made more complicated by the variation in underlying films or underlying structures that normally occurs within a wafer, from wafer-to-wafer, and from lot-to-lot in a wafer production environment. For lithography process monitoring (e.g., focus and/or exposure monitoring) one needs to identify changes in the scatterometry signature that can be uniquely correlated with the lithography process parameters that one wishes to monitor and control. If the scatterometry signatures that are to be compared come from scatterometry measurement features that differ significantly in process parameters or material properties other than the lithography process parameters, then it may be more difficult to uniquely identify the aspects or properties of the scatterometry signature(s) that are due to the lithography process parameters.

Furthermore, scatterometry may be used in-line on production wafers thus eliminating the need to stop production. That is, metrology tools based on scatterometry may be used to perform focus and/or exposure monitoring on product wafers to enable ongoing focus/exposure process control and to reduce the requirement for time-consuming FEM test wafers.

While this invention has been described in terms of several preferred embodiments, there are alterations, permutations, and equivalents, which fall within the scope of this invention.

For example, multiple measurement target groups may be placed within the same field to determine the effective process parameters within the field. This information may be used to determine deviations from ideal optical system. For example, variation of effective focus with in the field may be analyzed to find problems with wafer or reticle tilt, or aberrations of the stepper lens system. This information may be used determine corrections to the stepper to minimize the effects of the tilt or aberrations on the product wafer.

Furthermore, at least one of the scatterometry signals or spectra in the differential measurement may be taken from an unpatterned area of the wafer as for example an area with no resist (formed by an open mask area) or an area with full resist (formed by chrome mask area). For example, it may be useful to compare spectra from mostly resist structures (like contact-like scatterometry measurement structures or actual contact arrays) with spectra from unstructured resist areas (chrome on mask). In some cases, the grating structures because of their dimensions may not be patterned in the photo resist during exposure. In cases such as this, the scatterometry signal produced therefrom may be compared to a scatterometry signal taken from a full resist area of the wafer. In addition, it may be useful to compare spectra from mostly open structures (like isolated lines or post like scatterometry measurement structures or periodic gate resist device patterns) with spectra from areas where the resist has been removed by the lithography process (clear mask, dose to clear and develop).

Further still, although not discussed in great detail, it should be noted that the grating structures may be formed on various layers and under layers. In fact, the grating structures may be formed on previously formed underlying gratings structures (re-use space where grating targets may already exits). This is generally made possible when the underlying grating structures produce common mode disturbances in the overlying grating structure. The underlying gratings structures may for example be parallel to or perpendicular to the overlying grating structure. The underlying grating structure may be formed from various materials including but not limited to metals such as copper. In one implementation, a crossed grating (having lines with perpendicular orientation to the upper line grating) formed from copper is disposed underneath the overlying gratings structure. In another implementation, a parallel grating formed from copper is formed underneath the overlying grating structure. In both these cases, the "copper mirror" enables scatterometry on back-end layers where large unpatterned areas may violate process guidelines. In some cases it may be advantageous to ensure that the grating structures used to create the difference signal have the same overlay or alignment to the underlying grating to minimize the influence of overlay variation on the difference signal to improve sensitivity to focus and exposure.

Moreover, analysis of properties of difference spectra or difference signals may be done by fitting to a formula using the entire spectral range or one or more wavelength regions of the difference spectra. Alternatively, the complex data set of difference spectra for a variety of process conditions may be used as input into an expert system like a neural network to train the expert system to "learn" the relationships between properties of the difference spectra and the process conditions. The difference spectra data from the production wafers can then be analyzed by comparison to the baseline database (comprising difference spectra, properties of difference spectra, equations relating properties of difference spectra to process parameters, relationships between difference spectra and process parameters "learned" by a neural network system, and the like) to determine the "effective" process parameters used to produce the production wafer.

Other methods of comparison of two or more spectra may also be used instead of or in addition to subtraction. For instance, the comparison may be performed by dividing one spectrum by another spectrum. The use of subtraction to produce difference spectra in the examples shown above by way of illustration is not a limitation on the invention.

It should also be noted that there are many alternative ways of implementing the methods and apparatuses of the present invention.

For example, although the invention was primarily directed at photolithographic processes associated with semiconductor manufacturing, it should be noted that this is not a limitation. The invention described herein may be suitable for a wide variety of photolithographic processes, including but not limited to semiconductor manufacturing, optical device manufacturing, micro-mechanical device manufacturing, magnetic recording data storage manufacturing and the like. Additionally, while focus and exposure will be primarily discussed herein, it should be noted this is by way of example and not by way of limitation. Other process parameters that may be monitored include etch time, etch voltage bias, etch power, and the like.

t is therefore intended that the following appended claims be interpreted as including all such alterations, permutations, and equivalents as fall within the true spirit and scope of the present invention.

What is claimed is:

1. A method, comprising:

obtaining scatterometry signals by performing scatterometry measurements on a plurality of grating structures with different process responses, each grating structure having a first grating parameter and the grating structures having different values for the first grating parameter;

comparing scatterometry signals from said different grating structures in order to ascertain information about one or more process parameters used to form said grating structures; and controlling said one or more process parameters based on said comparison, wherein the differences between process responses are attributable at least in part to the differences between the different values for the first grating parameters and wherein the different values for the first grating parameters are selected so as to cause different process responses under the same process parameters.

2. The method as recited in claim 1 wherein the step of comparing comprises:

determining the difference between scatterometry signals from said plurality of grating structures.

3. The method as recited in claim 2 wherein the step of comparing further comprises:

determining the effective values of said one or more process parameters by comparing the difference between scatterometry signals to calibration data.

4. The method as recited in claim 3 wherein the step of controlling comprises:

controlling said one or more process parameters in accordance with the effective values of said one or more process parameters.

5. The method as recited in claim 3 wherein the calibration data is in the form of one or more equations, graphs or libraries.

6. The method as recited in claim 3 wherein the calibration comprises:

performing scatterometry measurements on a plurality of sets of grating structures with different process responses for varying process conditions;

calculating the difference between the scatterometry signals for each set of grating structures;

mapping the differences between the scatterometry signals for each set of grating structures as a function of the varying process conditions.

7. The method as recited in claim 2 wherein the step of comparing further comprises:

determining if the difference between scatterometry signals is within a predetermined control limit.

8. The method as recited in claim 7 wherein the step of controlling comprises:

controlling said one or more process parameters in accordance with whether or not the difference between scatterometry signals is within said predetermined control limit.

9. The method as recited in claim 2 wherein the different scatterometry signals are subtracted from one another in order to produce one or more difference signals.

10. The method as recited in claim 9 wherein one or more difference properties are obtained from the one or more difference signals.

11. The method as recited in claim 10 wherein the one or more difference signals or some property thereof are compared to calibration data in order to determine the effective values of one or more process parameters.

12. The method as recited in claim 1 further comprising:

forming said plurality of grating structures with different process responses on a wafer with a mask.

13. The method as recited in claim 1 further comprising:

designing a mask with two or more masking structures, each of which is configured to produce a grating structure that responds differently to one or more process parameters.

14. A method for controlling one or more process parameters, comprising:

obtaining scatterometry signals for a first grating structure with a first process response and a second grating structure with a second process response different from the first process response, each of the grating structures being configured with different sensitivities to one or more process parameters which are desired to be controlled;

comparing scatterometry signals of the first and second grating structures, each of the first and second grating structures producing different scatterometry signals for a given set of process parameters; and extracting information about one or more process parameters of the given set of process parameters based on said comparison, wherein the first grating structure and the second grating structure each has a first grating parameter and wherein a first value of the first grating structure's first grating parameter differs from a second value of the second grating structure's first grating parameter and wherein the difference between the first process response and the second process response is attributable at least in part to the difference between the first value and the second value.

15. A method of determining optimal or best focus, the method comprising:

forming a target group at a plurality of focus settings, the target group containing a plurality of targets with different sensitivities to focus, each target having a first parameter and the plurality of targets having different values for the first parameter, wherein the differences in sensitivities are attributable at least in part to the differences between the different values and wherein the different values are selected so as to cause different process responses under the same process parameters;

obtaining scatterometry signals for each of the targets in the target groups;

calculating difference signals for each target group;

forming a relationship between the difference signal or a property of the difference signal to the focus settings; and extracting optimal or best focus using the relationship.

16. The method as recited in claim 15 further comprising: calculating a property for each of the difference signals.

17. The method as recited in claim 16 wherein the property is calculated using root mean squared difference.

18. A process control method, comprising:

measuring two or more measurable patterns that are configured with different process responses so as to produce different scatterometry signals for a given set of process conditions, each pattern having a first parameter and the measurable patterns having different values for the first parameter; and extracting information about one or more process parameters associated with a photolithographic process by analyzing the differences between the different scatterometry signals from the measurable patterns for a given set of process conditions, wherein the differences between the process responses are attributable at least in part to the differences between the different values and wherein the different values are selected so as to cause different process responses under the same process conditions.

19. A target group, comprising:

a plurality of scatterometry targets configured to have different process responses, each target having a first parameter, the plurality of scatterometry targets having different values for the first parameter, the scatterometry targets with different process responses producing different scatterometry signals, the differences in the scatterometry signals being attributable at least in part to one or more process parameters used to create the scatterometry targets, wherein the differences between the process responses is attributable at least in part to the differences between the different values and wherein the different values are selected so as to cause different process responses under the same process conditions.

20. The target group as recited in claim 19 wherein the scatterometry targets are grating structures, a first grating structure including a first grating parameter having a first value formed from a first sensitivity to a process parameter, a second grating structure including the first grating parameter having a value formed from a second sensitivity to the process parameter.

21. The target group as recited in claim 20 wherein the second sensitivity is greater than or less than the first sensitivity.

22. The target group as recited in claim 20 wherein the grating structures are printed on the surface of a workpiece, the surface representing an exposed layer of photoresist, a partially developed layer of photoresist, a developed layer of photoresist, or an underlayer of the workpiece.

23. The target group as recited in claim 20 wherein the grating structures are located within the scribeline, device structure or within both the scribeline and the device structure.

24. The target group as recited in claim 20 wherein the grating structures are periodic in one direction or two directions.

25. The target group as recited in claim 20 wherein the first and second grating structures have the same pitch, but different linewidths or diameters.

26. The target group as recited in claim 20 wherein the grating structures are both positive tone or negative tone.

27. The target group as recited in claim 20 wherein at least one of the grating structures is a positive tone and the other is a negative tone.

28. The target group as recited in claim 20 wherein the first and second grating structures have the same pitch in both the x and y directions, but different optical proximity conections (OPC).

29. The target group as recited in claim 20 at least one of the grating structures includes segmented lines.

30. The target group as recited in claim 29 wherein the first and second grating structures have the same pitch, but different segment widths.

31. The target group as recited in claim 29 wherein the first and second grating structures have the same pitch, but different shape segments.

32. The method of claim 14, wherein the first grating structure and the second grating structure were formed under substantially the same process parameters.

33. The method of claim 18, wherein some of the patterns are formed under substantially the same process conditions and some of the targets are formed under substantially different process conditions.

* * * * *